(12) United States Patent
Kishore et al.

(10) Patent No.: US 9,901,624 B2
(45) Date of Patent: Feb. 27, 2018

(54) METHODS AND COMPOSITIONS FOR TREATING NEPHROGENIC DIABETES INSIPIDUS

(71) Applicants: Bellamkonda K. Kishore, Sandy, UT (US); Noel G. Carlson, Salt Lake City, UT (US); Donald E. Kohan, Salt Lake City, UT (US); Raoul D. Nelson, Salt Lake City, UT (US)

(72) Inventors: Bellamkonda K. Kishore, Sandy, UT (US); Noel G. Carlson, Salt Lake City, UT (US); Donald E. Kohan, Salt Lake City, UT (US); Raoul D. Nelson, Salt Lake City, UT (US)

(73) Assignees: The United States of America as represented by the Department of Veterans Affairs, Washington, DC (US); The University of Utah, Salt Lake City, UT (US)

( * ) Notice: Subject to any disclaimer, the term of this patent is extended or adjusted under 35 U.S.C. 154(b) by 0 days.

(21) Appl. No.: 14/305,999

(22) Filed: Jun. 16, 2014

(65) Prior Publication Data

US 2017/0035859 A1   Feb. 9, 2017

Related U.S. Application Data

(63) Continuation of application No. 11/666,141, filed as application No. PCT/US2005/038231 on Oct. 21, 2005, now abandoned.

(60) Provisional application No. 60/621,910, filed on Oct. 25, 2004.

(51) Int. Cl.

| | |
|---|---|
| A61K 38/46 | (2006.01) |
| A61K 31/185 | (2006.01) |
| A61K 31/53 | (2006.01) |
| A61K 31/675 | (2006.01) |
| A61K 31/00 | (2006.01) |
| A61K 31/192 | (2006.01) |
| A61K 31/365 | (2006.01) |
| A61K 31/405 | (2006.01) |
| A61K 31/4965 | (2006.01) |
| A61K 31/5575 | (2006.01) |
| A61K 31/7072 | (2006.01) |
| A61K 31/7076 | (2006.01) |
| A61K 45/06 | (2006.01) |
| A61K 31/18 | (2006.01) |
| A61K 31/549 | (2006.01) |

(52) U.S. Cl.
CPC ............. *A61K 38/46* (2013.01); *A61K 31/00* (2013.01); *A61K 31/18* (2013.01); *A61K 31/185* (2013.01); *A61K 31/192* (2013.01); *A61K 31/365* (2013.01); *A61K 31/405* (2013.01); *A61K 31/4965* (2013.01); *A61K 31/53* (2013.01); *A61K 31/549* (2013.01); *A61K 31/5575* (2013.01); *A61K 31/675* (2013.01); *A61K 31/7072* (2013.01); *A61K 31/7076* (2013.01); *A61K 45/06* (2013.01); *C12Y 306/01005* (2013.01)

(58) Field of Classification Search
None
See application file for complete search history.

(56) References Cited

U.S. PATENT DOCUMENTS

2003/0149113 A1   8/2003   Caplan et al.

OTHER PUBLICATIONS

Abbracchio et al. (2003). TRENDS in Pharmacological Sciences. 24(2):52-55.*
Libber et al. (1986). J. Pediatr. 108(2):305-311 (Abstract Only).*
Abe, M. "A case of diabetes insipidus treated with germain (bayer 205)," *Tohoku J. Exp. Med.*, 1965, 62:128.
Agre, P., "Aquaporin water channels in kidney," *J Am Soc Nephrol*, 2000, 11:764-77.
Bao, Y. et al., "Prostaglandin transporter PGT is expressed in cell types that synthesize and release prostanoids," *Am J Physiol Renal Physiol*, 2002, 282:F1103-10.
Bell, T. N., "Diabetes insipidus," *Crit Care Nurs Clin North Am*, 1994, 6:675-85.
Bonventre, J. V., "Phospholipase A2 and signal transduction," *J Am Soc Nephrol*, 1992, 3:128-50.
Bonventre, J. V. and R. Nemenoff, "Renal tubular arachidonic acid metabolism," *Kidney Int*, 1991, 39:438-49.
Breyer, M. D. and R. M. Breyer, "Prostaglandin E receptors and the kidney," *Am J Physiol Renal Physiol*, 2000, 279:F12-23.
Chou, C. L. et al., "Phosphoinositide signaling in rat inner medullary collecting duct," *Am J Physiol*, 1998, 274:F564-72.
Communi, D. et al., "Advances in signalling by extracellular nucleotides. The role and transduction mechanisms of P2Y receptors," *Cell Signal*, 2000, 12:351-60.
DiGiovanni, S. R. et al., "Regulation of collecting duct water channel expression by vasopressin in Brattleboro rat," *Proc Natl Acad Sci USA*, 1994, 91:8984-88.
Di Renzo, G. C. et al., "Phosphatidylinositol-specific phospholipase C in fetal membranes and uterine decidua," *J Clin Invest*, 1981, 67:847-56.
Ecelbarger, C. A. et al., "Extracellular ATP increases intracellular calcium in rat terminal collecting duct via a nucleotide receptor," *Am J Physiol*, 1994, 267:F998-1006.
Ecelbarger, C. A. et al., "Expression of salt and urea transporters in rat kidney during cisplatin-induced polyuria," *Kidney Int*, 2001, 60:2274-82.
Ecelbarger, C. A. et al., "Decreased renal Na—K—2Cl costransporter abundance in mice with heterozygous disruption of the G(s)alpha gene," *Am J Physiol*, 1999, 277:F235-44.
Endo, S. et al., "Expression of PGT in MDCK cell monolayers: polarized apical localization and induction of active PG transport," *Am J Physiol Renal Physiol*, 2002, 282:F618-22.

(Continued)

*Primary Examiner* — Christine J Saoud
*Assistant Examiner* — Jon M Lockard
(74) *Attorney, Agent, or Firm* — Adriano & Associates

(57) ABSTRACT

Disclosed are compositions and methods for treating nephrogenic diabetes insipidus and for induction of diuretic effect.

22 Claims, 15 Drawing Sheets

(56) References Cited

OTHER PUBLICATIONS

Enjyoji, K. et al., "Targeted disruption of cd39/ATP diphosphohydrolase results in disordered hemostasis and thromboregulation," *Nat Med*, 1999, 5:1010-17.

Erb, L. et al., "Site-directed mutagenesis of P2U purinoceptors. Positively charged amino acids in transmembrane helices 6 and 7 affect agonist potency and specificity," *J Biol Chem*, 1995, 270:4185-88.

Fradet, Y. et al., "Enhanced urinary prostaglandin E2 in postobstructive diuresis in humans," *Prostaglandins Med*, 1980, 5:29-30.

Fradet, Y. et al., "Renal prostaglandins in postobstructive diuresis. Comparative study of unilateral and bilateral obstruction in conscious dogs," *Prostaglandin Leukot Essent Fatty Acids*, 1988, 31:123-29.

Frøkiaer, J. et al., "Bilateral ureteral obstruction downregulates expression of vasopressin-sensitive AQP-2 water channel in rat kidney," *Am J Physiol*, 1996, 270:F657-68.

Frøkiaer, J. et al., "Pathophysiology of aquaporin-2 in water balance disorders," *Am J Med Sci*, 1998, 316:291-9.

Frøkiaer, J. et al., "Low aquaporin-2 level in polyuric DI +/+ severe mice with constitutively high cAMP-phosphodiesterase activity," *Am J Physiol*, 1999, 276:F179-90.

Garcia-Villalba, P. et al., "Real-time PCR quantification of AT1 and AT2 angiotensin receptor mRNA expression in the developing rat kidney," *Nephron Exp Nephrol*, 2003, 94:e154-59.

Gitlin, M., "Lithium and the kidney: an updated review," *Drug Saf*, 1999, 20:231-43.

Han, J. S. et al., "Vasopressin-independent regulation of collecting duct water permeability," *Am J Physiol*, 1994, 266:F139-46.

Homma, S. et al., "Role of cAMP-phosphodiesterase isozymes in pathogenesis of murine nephrogenic diabetes insipidus," *Am J Physiol*, 1991, 261:F345-53.

Hozawa, S. et al., "cAMP motifs regulating transcription in the aquaporin 2 gene," *Am J Physiol*, 1996, 270:C1695-702.

Inscho, E. W., "Renal microvascular effects of P2 receptor stimulation," *Clin Exp Pharmacol Physiol*, 2001, 28:332-39.

Ivanov, A. I. et al., "Prostaglandin E(2)-synthesizing enzymes in fever: differential transcriptional regulation," *Am J Physiol Regul Integr Comp Physiol*, 2002, 283:R1104-17.

Kishore, B. K. et al., "Extracellular nucleotide receptor inhibits AVP-stimulated water permeability in inner medullary collecting duct," *Am J Physiol*, 1995, 269:F863-69.

Kishore, B. K. et al., "Cellular localization of P2Y(2) purinoceptor in rat renal inner medulla and lung," *Am J Physiol Renal Physiol*, 2000, 278:F43-51.

Kishore, B. K. et al., "Expression of renal aquaporins 1, 2 and 3 in a rat model of cisplatin-induced polyuria," *Kidney Int*, 2000, 58:701-11.

Kishore, B. K. et al., "P2Y2 receptor mRNA and protein expression is altered in inner medullae of hydrated and dehydrated rats: Relevance to AVP-independent regulation of IMCD function," *Am J Physiol Renal Physiol*, 2005, 288:F1164-F1172.

Kishore, B. K. et al., "Quantitation of aquaporin-2 abundance in microdissected collecting ducts: axial distribution and control by AVP," *Am J Physiol*, 1996, 271:F62-70.

Kohan, D. E. and K. Hughe, "Autocrine role of endothelin in rat IMCD: Inhibition of AVP induced cAMP accumulation," *Am J Physiol Renal Physiol*, 1993, 265:F126-F129.

Koyamada, N. et al., "Apyrase administration prolongs discordant xenograft survival," *Transplantation*, 1996, 62:1739-43.

Krane, C. M. et al., "Aquaporins: the membrane water channels of the biological world," *Biologist*, 2003, 50:81-8.

Kwon, T. H. et al., "Altered expression of renal AQPs and Na(+) transporters in rats with lithium-induced NDI," *Am J Physiol Renal Physiol*, 2000, 279:F552-64.

László, K. et al., "Prostaglandin-dependent changes in renal haemodynamics and excretory patterns before and after release of 24 hours bilateral ureteral ligation," *Acta Physiol Acad Sci Hung*, 1980, 56:309-23.

Laycock, J. F. et al., "From vasopressin receptor to water channel: intracellular traffic, constraint and by-pass," *J Endocrinol*, 1998, 159:361-72.

Lenox, R. H. et al., "Neurobiology of lithium: an update," *J Clin Psychiatry*, 1998, 59 Supp:37-47.

Letsinger, R. L. et al., "Cholesteryl-conjugated oligonucleotides: synthesis, properties, and activity as inhibitors of replication of human immunodeficiency virus in cell culture," *Proc Natl Acad Sci USA*, 1989, 86:6553-56.

Li, C. et al., "Altered expression of urea transporters in response to ureteral obstruction," *Am J Physiol Renal Physiol*, 2004, 286:F1154-62.

Li, C. et al., "Altered expression of major renal Na transporters in rats with unilateral ureteral obstruction," *Am J Physiol Renal Physiol*, 2003, 284:F155-66.

Lin, L. L., "cPLA2 is phosphorylated and activated by MAP kinase," *Cell*, 1993, 72:269-78.

Marples, D. et al., "Lithium-induced downregulated of aquaporin-2 water channel expression in rat kidney medulla," *J Clin Invest*, 1995, 95:1838-45.

Matsumura, Y. et al., "Transcriptional regulation of aquaporin-2 water channel gene by cAMP," *J Am Soc Nephrol*, 1997, 8:861-67.

McHowat, J. et al., "Thrombin activates a membrane-associated calcium-independent PLA2 in ventricular myocytes," *Am J Physiol*, 1998, 274:C447-54.

Moses, A. M. et al., "Evidence for normal antidiuretic responses to endogenous and exogenous arginine vasopressin in patients with guanine nucleotide-binding stimulatory protein-deficient pseudohypoparathyroidism," *J Clin Endocrinol Metab*, 1986, 62:221-24.

Murray, M. D. et al., "Renal toxicity of the nonsteroidal anti-inflammatory drugs," *Annu Rev Pharmacol Toxicol*, 1993, 33:435-65.

Murthy, K. S. et al., "PKA-dependent activation of PDE3A and PDE4 and inhibition of adenylyl cyclase V/VI in smooth muscle," *Am J Physiol Cell Physiol*, 2002, 282:C508-17.

Nadler, S. P. et al., "PGE2 inhibits water permeability at a post-cAMP site in rat terminal inner medullary collecting duct," *Am J Physiol*, 1992, 262:F229-35.

Nielsen, S. et al., "Vasopressin increases water permeability of kidney collecting duct by inducing translocation of aquaporin-CD water channels to plasma membrane," *Proc Natl Acad Sci USA*, 1995, 92:1013-1017.

Nielsen, S. et al., "Cellular and subcellular immunolocalization of vasopressin-regulated water channel in rat kidney," *Proc Natl Acad Sci USA*, 1993, 90:11663-67.

Nielsen, S. et al., "Physiology and pathophysiology of renal aquaporins," *J Am Soc Nephrol*, 1999, 10:647-63.

Nishizuka, Y. et al., "Intracellular signaling by hydrolysis of phospholipids and activation of protein kinase C," *Science*, 1992, 258:607-14.

Oksche, A. and W. Rosenthal, "The molecular basis of nephrogenic diabetes insipidus," *J Mol Med*, 1998, 76:326-37.

Ostrom, R. S. et al., "Stoichiometry and compartmentation in G protein-coupled receptor signaling: implications for therapeutic interventions involving G(s)," *J Pharmacol Exp Ther*, 2000, 294:407-12.

Phelan, K. M. et al., "Lithium interaction with the cyclooxygenase 2 inhibitors rofecoxib and celecoxib and other nonsteroidal anti-inflammatory drugs," *J Clin Psychiatry*, 2003, 64:1328-34.

Ralevic, V. and G. Burnstock, "Receptors for purines and pyrimidines," *Pharmacol Rev*, 1998, 50:413-92.

Rice, W. R. et al., "Cloning and expression of the alveolar type II cell P2u-purinergic receptor," *Am J Respir Cell Mol Biol*, 1995, 12:27-32.

Roman, R. J. and C. Lechene, "Prostaglandin E2 and F2 alpha reduces urea reabsorption from the rat collecting duct," *Am J Physiol*, 1981, 241:F53-60.

Rouch, A. J. and L. H. Kudo, "Role of PGE(2) in alpha(2)-induced inhibition of AVP- and cAMP-stimulated H(2)O, Na(+), and urea transport in rat IMCD," *Am J Physiol Renal Physiol*, 2000, 279:F294-301.

(56) References Cited

OTHER PUBLICATIONS

Rouse, D. et al., "ATP inhibits the hydrosmotic effect of AVP in rabbit CCT: evidence for a nucleotide P2u receptor," *Am J Physiol*, 1994, 267:F289-95.

Schweibert, E. M. and B. K. Kishore, "Extracellular nucleotide signaling along the renal epithelium," *Am J Physiol Renal Physiol*, 2001, 280:F945-63.

Sheikh-Hamad, D. et al., "Cellular and molecular studies on cisplatin-induced apoptotic cell death in rat kidney," *Arch Toxicol*, 2004, 78:147-55.

Shoji, Y. et al., "Downregulation of prostaglandin E receptor subtype EP3 during colon cancer development," *Gut*, 2004, 53:1151-58.

Sonnenberg, H. and D. R. Wilson, "The role of the medullary collecting ducts in postobstructive diuresis," *J Clin Invest*, 1976, 57:1564-74.

Sugawara, M. et al., "Involvement of prostaglandin E2, cAMP, and vasopressin in lithium-induced polyuria," *Am J Physiol*, 1988, 254:R863-69.

Sun, R. et al., "P2Y2 receptor-mediated release of prostaglandin E2 by IMCD is altered in hydrated and dehydrated rats: relevance to AVP-independent regulation of IMCD function," *Am J Physiol Renal Physiol*, 2005, 289:F585-92.

Sun, R. et al., "Chronic dDAVP infusion in rats decreases the expression of P2Y2 receptor in inner medulla and P2Y2 receptor-mediated PGE2 release by IMCD," *Am J Physiol Renal Physiol*, 2005, 289:F768-76.

Takeda, S. et al., "High activity of low-Michaelis-Menten constant 3',5'-cyclic adenosine monophosphate-phosphodiesterase isozymes in renal medulla of mice with hereditary nephrogenic diabetes insipidus," *Endocrinology*, 1991, 129:287-94.

Teitelbaum, I., "Hormone signaling systems in inner medullary collecting ducts," *Am J Physiol*, 1992, 263:F985-90.

Terris, J. et al., "Long-term regulation of renal urea transporter protein expression in rat," *J Am Soc Nephrol*, 1998, 9:729-36.

Timmer, R. T. and J. M. Sands, "Lithium intoxication," *J Am Soc Nephrol*, 1999, 10:666-74.

Vallon, V., "P2 receptors in the regulation of renal transport mechanisms," *Am J Physiol Renal Physiol*, 2008, 294:F10-27.

Van Rhee, A. M. et al., "Modelling the P2Y purinoceptor using rhodopsin as template," *Drug Des Discov*, 1995, 13:133-54.

Wang, W. et al., "AQP3, p-AQP2, and AQP2 expression is reduced in polyuric rats with hypercalcemia: prevention by cAMP-PDE inhibitors," *Am J Physiol Renal Physiol*, 2002, 283:F1313-25.

Welch, B. D. et al., "P2Y2 receptor-stimulated release of prostaglandin E2 by rat inner medullary collecting duct preparations," *Am J Physiol Renal Physiol*, 2003, 285:F711-21.

Williams, M., "Purines: from premise to promise," *J Auton Nerv Syst*, 2000, 81:285-28.

Yang, T. et al., "Regulation of cyclooxygenase-2 expression in renal medulla by tonicity in vivo and in vitro," *Am J Physiol*, 1999, 277:F1-9.

Yasui, M. et al., "Adenylate cyclase-coupled vasopressin receptor activates AQP2 promoter via dual effect on CRE and AP1 elements," *Am J Physiol*, 1997, 272:F443-50.

Zelenina, M. et al., "Prostaglandin E(2) interaction with AVP: effects on AQP2 phosphorylation and distribution," *Am J Physiol Renal Physiol*, 2000, 278:F388-94.

\* cited by examiner

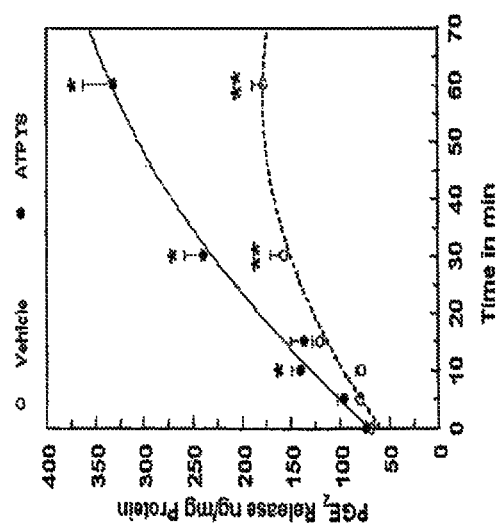
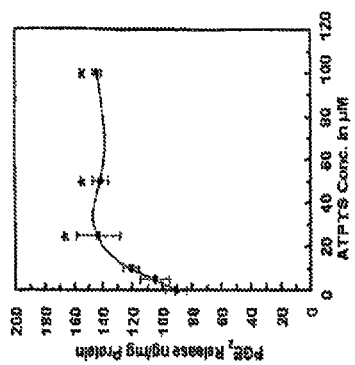
FIG. 3A
FIG. 3B

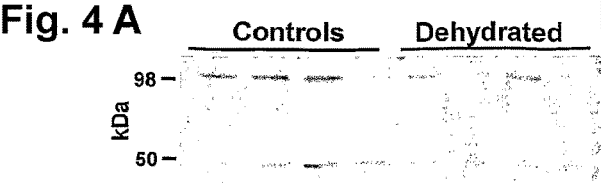
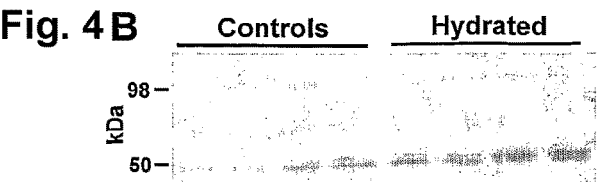
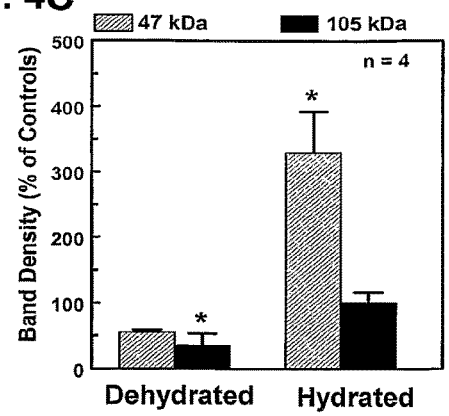
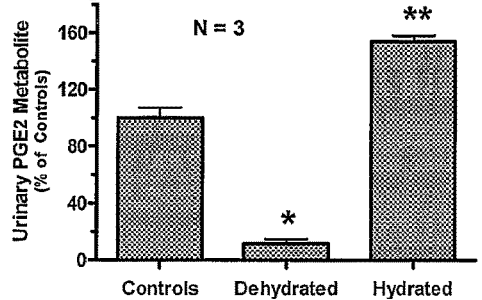
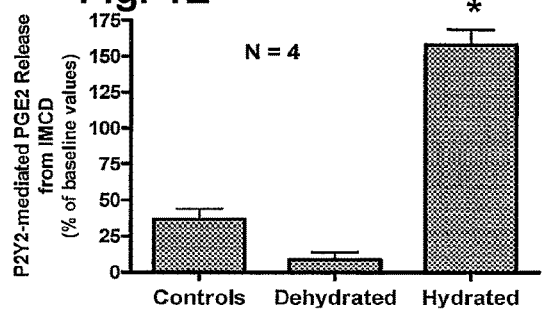
Figure 4 A-E

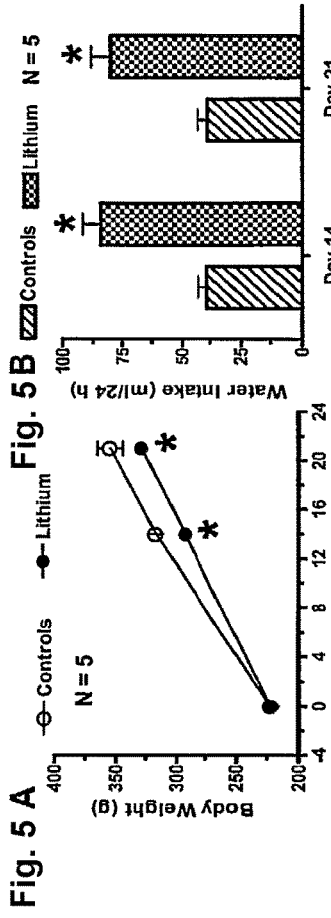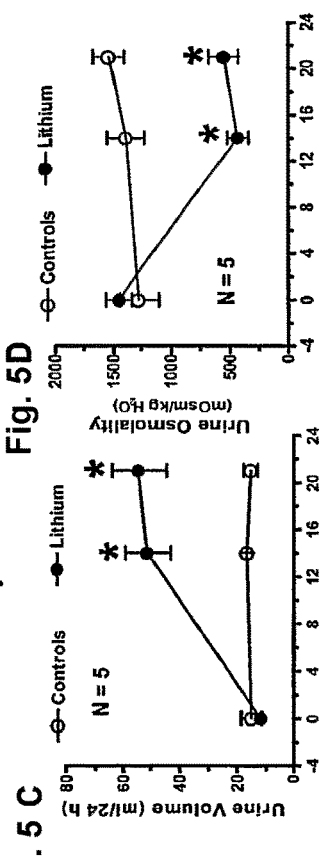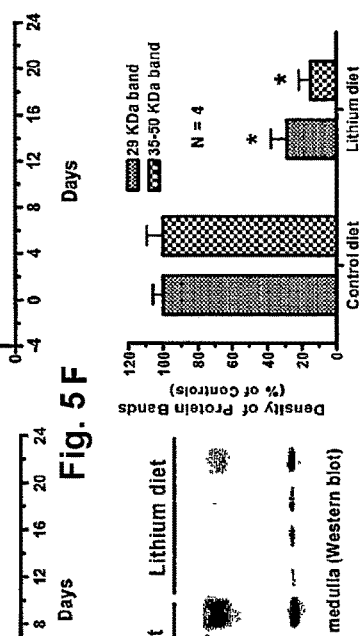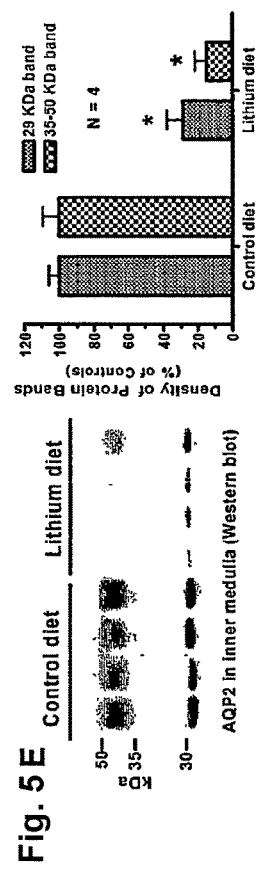
FIG. 5 A-F

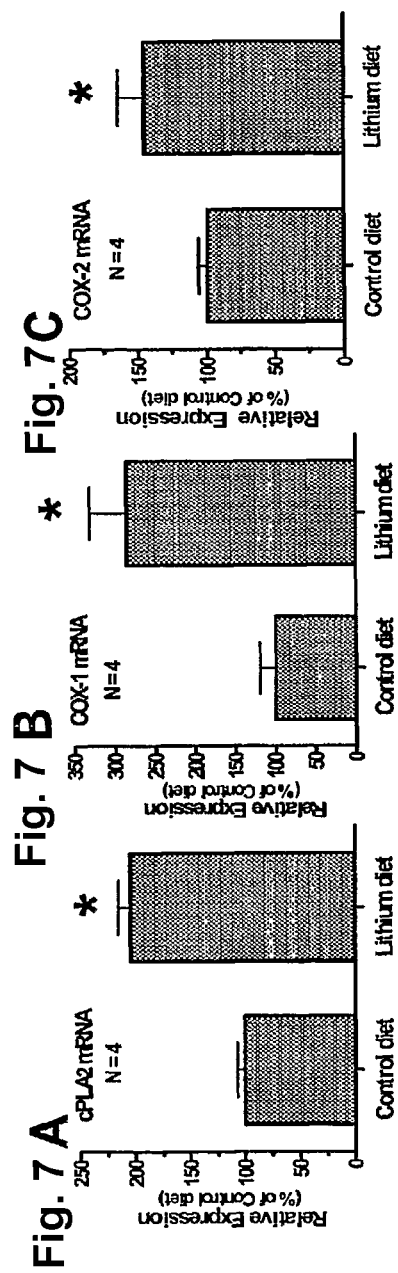
FIG. 7 A-C

Figure 8 A-F

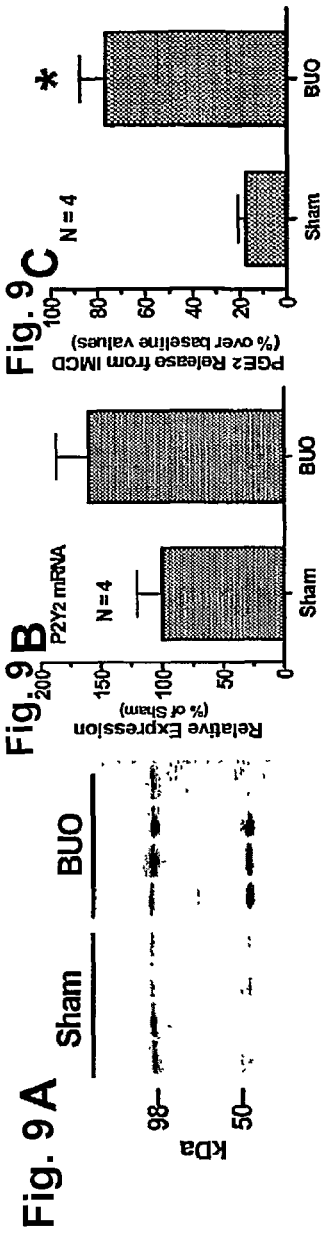
FIG. 9 A-C

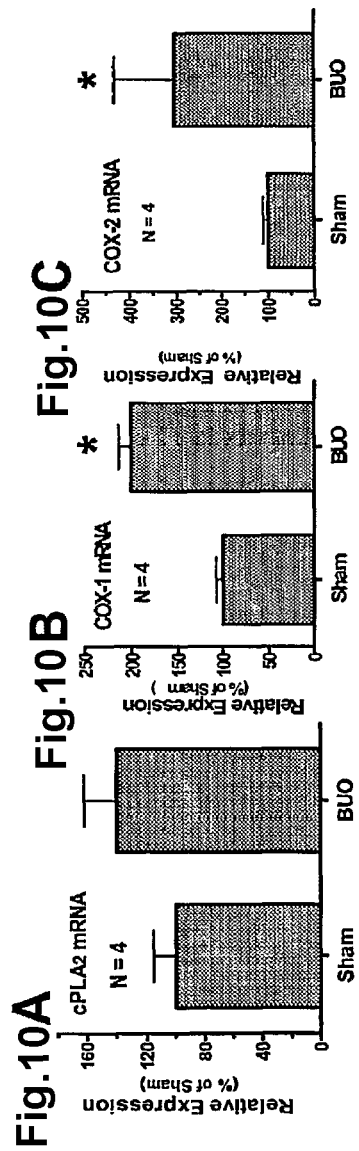
FIG. 10 A-C

METHODS AND COMPOSITIONS FOR TREATING NEPHROGENIC DIABETES INSIPIDUS

CROSS REFERENCE TO RELATED APPLICATION

This application is a continuation application of U.S. Ser. No. 11/666,141, filed Aug. 6, 2008, which is a 35 U.S.C. § 371 application of PCT Application No. PCT/US2005/038231, filed Oct. 21, 2005, and claimed priority to U.S. Provisional Application 60/621,910, filed on Oct. 25, 2004 by Bellamkonda K. Kishore, Noel Carlson, Donald Kohan, and Raoul Nelson, and this application is incorporated herein in its entirety by reference.

STATEMENT REGARDING FEDERALLY SPONSORED RESEARCH

This invention was made possible with the facilities and resources at the VA Salt Lake City Health Care System. This invention was also made with government support under federal grants DK61183 DK58953, and 53990 awarded by the NIH. Therefore, the United States Government may have certain rights in this invention.

SUMMARY

As embodied and broadly described herein, the disclosed compositions and methods, in one aspect, relate to the treatment of nephrogenic diabetes insipidus (NDI). This application also relates to the use of P2Y2 agonists as diuretics. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several embodiments of the compositions and methods and together with the description, serve to explain the principles of the compositions and methods.

FIGS. 3A and 3B show the release of PGE2 by the agonist stimulation of P2Y2 receptor. FIG. 3A shows time-course of release of PGE2 by the agonist stimulation of P2Y2 receptor in rat IMCD preparations in vitro. Freshly prepared IMCD-enriched fractions were incubated at 37.degree. C. under physiological conditions in the absence (vehicle, .small-circle.) or presence (.endot.) of 100.mu.M of ATP.gamma.S for different periods of time. PGE2 released into the medium was assayed by EIA and normalized to the protein content of the incubations. Results are expressed as mean.+-.SEM of triplicate incubations. *significantly different from the corresponding vehicle alone incubations, **significantly different from the corresponding 0, 5 and 10 min values. FIG. 3B shows concentration-response curve for the release of PGE2 by the agonist stimulation of P2Y2 receptor in rat IMCD preparations in vitro. Freshly prepared IMCD-enriched fractions were incubated at 37.degree. C. for 10 min with increasing concentrations of ATP.gamma.S (0-100.mu.M). PGE2 released into the medium was assayed by EIA and normalized to the protein content of the incubations. Results are mean.+-.SEM of triplicate incubations. *significantly different from the 0.mu.M ATP.gamma.S incubations.

FIGS. 4A, 4B, 4C, 4D, and 4E show purinergic and prostanoid interactions in the inner medulla of hydrated and dehydrated rats. Animal model: Hydration and dehydration of rats was achieved by either adding sucrose (600 mM) to drinking water or by depriving drinking water, respectively, for 2 days prior to euthanasia. Control rats received plain tap water. All rats had free access to standard rat chow. Urine samples were collected from rats by housing them in individual metabolic cages during the last 24 hours of experimental period. Twenty-four hour urine volumes and osmolality were determined. Hydrated rats had high urine output of very dilute urine and dehydrated rats had low output of concentrated urine Panels A-C: Altered protein abundance of P2Y2 receptor in the inner medulla of hydrated and dehydrated rat kidneys. Whole tissue homogenates were prepared, solubilized and immunoblotted for P2Y2 protein. The P2Y2 receptor antibody identifies two sets of immunoreactive bands in the kidney (Kishore et al, 2000a) (panels A & B). Both 47 kDa and 105 kDa bands are specific, as these were ablated by pre-adsorption of the antibody with the immunizing peptide. Blots were digitized, band densities determined, and expressed as percent of mean values in controls (panel C). Numerical results are expressed as mean±SEM. *significantly different from the corresponding band in the other group. Panel D: Urinary excretion of PGE2 metabolites in control, hydrated and dehydrated rats. Groups of male rats (N=3 per group) were subjected to hydration and dehydration. Twenty-four hour urine samples were collected and assayed for PGE2 metabolite, using a commercial kit (Cayman Chemical Co, Ann Arbor, Mich.). This assay converts all the immediate PGE2 metabolites to a single, stable derivative that could be easily quantified by EIA. Measured urinary excretion of PGE2 metabolite values (ng/24 hours) are expressed as percent of mean values in the control group. *significantly different from the other two groups. **significantly different from the control group. Panel E: In vitro IMCD response to purinergic-stimulated PGE2 release in control, hydrated and dehydrated rats. Groups of rats (N=3 per group) were subjected to dehydration and hydration. Inner medullae from each group were pooled, and fractions enriched in IMCD were prepared from those pools by collagenase and hyaluronidase digestion (Welch et al, 2003). The pooled IMCD preparations from each group was divided into two sets of tubes (N=4 per set). One set served as vehicle control (baseline value), while the other set of preparations was challenged with 50 µM of ATPγS (a non-hydrolyzable agonist of P2Y2 receptor) for 20 min at 37° C. The fraction was arrested by adding chilled incubation buffer. Samples were centrifuged to pellet IMCD, and the PGE2 concentration in the supernatants was assayed by a commercial EIA kit and normalized to the protein content of the incubations (ng/mg protein). ATP.gamma.S-stimulated release of PGE2 in each group was computed as percent increase over the respective vehicle controls (baseline values). Results are expressed as mean.+-.SEM. *significantly different from the other two groups. The PGE2 release from the IMCD of dehydrated rats is significantly lower than that of controls.

FIGS. 5A, 5B, 5C, 5D, 5E, and 5F show characterization of rat model of lithium-induced NDI. Panel A: Body weights of rats fed control or lithium-added diets. Panel B. Water intake in rats fed control or lithium-added diets. Panel C: Twenty-four hour-urine volumes in rats fed control or lithium-added diets. Panel D: Urine osmolalities in rats fed control or lithium-added diets. Panel E: Protein abundance of AQP2 water channel in the inner medulla of rats fed control or lithium-added diets, as determined by Western blotting. Panel F: Densitometry of AQP2 protein bands in rats fed control or lithium-added diets. Results are expressed as mean.+−.SEM. *significantly different from the corresponding value in control diet group.

FIGS. 7A, 7B, and 7C show expression of cytosolic phospholipase A2 (cPLA2; panel A), cyclooxygenase-1 (COX-1; panel B) and cyclooxygenase-2 (Cox-2; panel C) messenger RNA in the renal inner medulla of rats led control or lithium added diets for 21 days. Messenger mRNA extraction, purification, reverse transcription, real-time PCR amplifications and computation of results were carried out as described for P2Y2 receptor in FIG. 6 legend. The sequences of primer pairs used in these amplifications are shown in Table 6. The expression of cPLA2, COX-1 and COX-2 genes was normalized to the expression of housekeeping gene .beta.-actin (Relative Expression), and computed as percent or mean values in the control diet group. Results are mean.+−.SEM. *significantly different from the control diet group. Lithium diet fed rats showed approximately 2-, 3- and 1.5-fold increase in mRNA expression of cPLA2, COX-1 and COX-2 as compared to the control diet fed group.

FIGS. 9A, 9B, and 9C show protein abundance (panel A) and mRNA expression (panel B) of P2Y2 receptor in the inner medulla, and in vitro IMCD response to purinergic-stimulated PGE2 release (panel C) in sham operated and BUO rats. Sham operated (N=2) and BUO (N=3) rats were euthanized on day 7. Inner medullae from sham operated and BUO rats were pooled separately, and fractions enriched in IMCD were prepared from these pools by collagenase and hyaluronidase digestion. Experiments were carried out as described for hydrated and dehydrated rats in FIG. 4. ATP.gamma.S-stimulated release of PGE2 in group was computed as percent increase over the respective vehicle controls (baseline values). Results are expressed as mean.+−.SEM of four incubations from pooled IMCD in each group. *significantly different from the sham operated group. The mean increase in P2Y2-stimulated release of PGE2 in BUO rats is about 4.3-fold higher as compared to the mean increase in sham operated controls.

FIGS. 10A, 10B, and 10C show expression of cytosolic phospholipase A2 (cPLA2; panel A), cyclooxygenase-1 (COX-1; panel B) and cyclooxygenase-2 (Cox-2; panel C) mRNA in the renal inner medulla of sham operated and BUO rats. Messenger mRNA extraction, purification, reverse transcription, real-time PCR amplifications and computation of results are carried out as described for P2Y2 receptor in FIG. 6 legend. The sequences of primer pairs used in these amplifications are shown in Table 6. The expression of cPLA2, COX-1 and COX-2 genes was normalized to the expression of housekeeping gene .beta.-actin (Relative Expression), and computed as percent or mean values in the control diet group. Results are mean.+−.SEM. *significantly different from the sham operated group. BUO rats showed approx. 2-, and 3-fold increase in mRNA expression of COX-1 and COX-2 as compared to the sham operated group.

DETAILED DESCRIPTION

Figure 1:
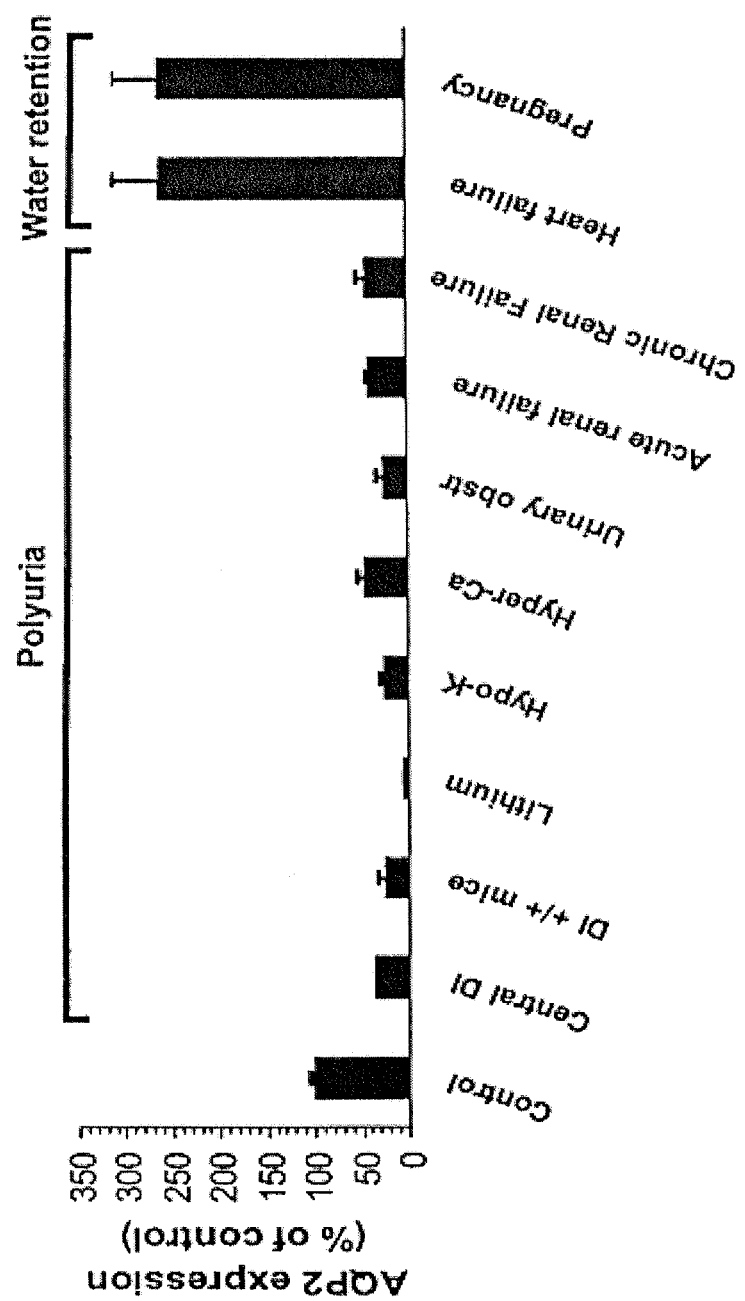
FIG. 1 shows water balance disorders associated with altered expression of vasopressin-regulated collecting duct water channel AQP2. As shown here, AQP2 protein expression is reduced, sometimes dramatically, in a wide variety of hereditary and acquired forms of diabetes insipidus characterized by varying degrees of polyuria. On the other hand, water retention conditions like heart failure and pregnancy are associated with increased expression of AQP2 protein. (Nielsen, et al. 1999).

The present compositions and methods can be understood more readily by reference to the following detailed description and the Examples included therein and to the Figures and their previous and following description.

Before the present compounds, compositions, articles, devices, and/or methods are disclosed and described, it is to be understood that the compositions and methods are not limited to specific synthetic methods, specific recombinant biotechnology methods unless otherwise specified, or to particular reagents unless otherwise specified, as such can, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for examples reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that die particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

"Optional" or "optionally" means that the subsequently described event or circumstance may or may not occur, and that the description includes instances where said event or circumstance occurs and instances where it does not.

The terms "higher," "increases," "elevates," or "elevation" refer to increases above basal levels, e.g., as compared to a control. The terms "low," "lower," "reduces," or "reduction" refer to decreases below basal levels, e.g., as compared to a control. For example, basal levels are normal in vivo levels prior to, or in the absence of, addition of an agent.

"Kidney cells" include all renal tubular epithelial cells, renal cortical tubules, glomerular cells, mesangial cells, interstitial cells, collecting duct principal cells, and intercalated cells of the kidney.

The term "diabetes insipidus" includes, but is not limited to, any disease of the kidneys such as neurogenic, also known as central, hypothalamic, pituitary, or neurohypophyseal diabetes; nephrogenic, also known as vasopressin-resistant; gestanic; and dipsogenic diabetes.

The term "test compound" is defined as any compound to be tested for its ability to interact with a selected cell, e.g., a P2Y antagonist. Examples of test compounds include, but are not limited to, suramin, acid blue 129, and acid blue 80. Also, "test components" include drugs, molecules, and compounds that come from combinatorial libraries where thousands of such ligands are screened by drug class.

The terms "control levels" or "control cells" are defined as the standard by which a change is measured, for example, the controls are not subjected to the experiment, but are instead subjected to a defined set of parameters, or the controls are based on pre- or post-treatment levels.

Throughout this application, various publications are referenced. The disclosures of these publications in their entireties are hereby incorporated by reference. The references disclosed are also individually and specifically incorporated by reference, herein lot the material contained in them that is discussed in the sentence in which the reference is relied upon.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, my subset or combination of these is also disclosed. Thus, for example, the sub-group of A-E, B-F, and C-E would be considered disclosed. This concept applies to all aspects of this application including, but not limited to steps in methods of making and using the disclosed compositions. Thus, if there are a variety of additional steps that can be performed it is understood that each of these additional steps can be performed with any specific embodiment or combination of embodiments of the disclosed methods.

B. Compositions and Methods

Acquired nephrogenic diabetes insipidus (NDI), which is relatively common, comprises several clinical conditions, such as lithium-induced nephropathy, hypokalemic nephropathy, hypercalcemia, and post-obstructive uropathy. The hallmark of these conditions is low protein levels of vasopressin-regulated water channel AQP2 in the medullary collecting duct, in the presence of normal or elevated circulating levels of arginine vasopressin (AVP). In both human patients and in experimental animals with acquired NDI, the production of renal prostaglandins such as PGE2, is increased. PGE2, by virtue of its ability to antagonise AVP-stimulated water permeability via retrieval of AQP2 water channels from the apical membrane of inner medullary collecting duct (IMCD), is involved in the development of polyuria of acquired NDI. Accordingly, inhibition of PGE2 synthesis by the administration of indomethacin was shown to ameliorate the polyuria of acquired NDI. In rat IMCD, agonist stimulation of P2Y2 purinergic (nucleotide) receptor results in production and release of PGE2 (Welch et al, 2003), and this response is markedly enhanced in hydrated polyuric rats (Sun et al, 2004). It has been shown that the purinergic-mediated PGE2 release in IMCD is also markedly enhanced in acquired NDI induced by lithium (Li) administration or by bilateral ureteral obstruction (BUO) and release. And this is associated with significant increases in mRNA expression of cyclooxygenases-1 and -2 in inner medulla of acquired NDI rats.

Diabetes insipidus (DI) causes considerable morbidity and inconvenience to the patients. Patients with DI, especially those critically ill, are at higher risk of dehydration, hypernatremia, alterations in the level of consciousness, and hemodynamic instability from hypovolemia, for example (Bell, 1994). Acquired nephrogenic diabetes insipidus (NDI), the more common form of NDI, can occur at any age. The most common cause of acquired NDI is lithium administration for the treatment of bipolar disorder. Other drugs that are capable of inducing acquired NDI are colchicine, methoxyflurane, amphotericin B, gentamicin, loop diuretics, and demeclocycline, for example. In addition to drugs, acquired NDI can also occur as a result of certain diseases. These include, but are not limited to chromic kidney diseases, hypokalemia, hypercalcemia, sickle cell disease, ureteral obstruction (obstructive uropathy), and low protein diet. The hallmark of these conditions, as documented in animal models, is low protein abundance of AVP-regulated water channel AQP2 in the medullary collecting duct in the face of normal or elevated circulating levels of AVP (Nielsen et al, 1999; FIG. 1). Thus, in these conditions, it appears that the inherent defect lies in the collecting duct.

Figure 2:
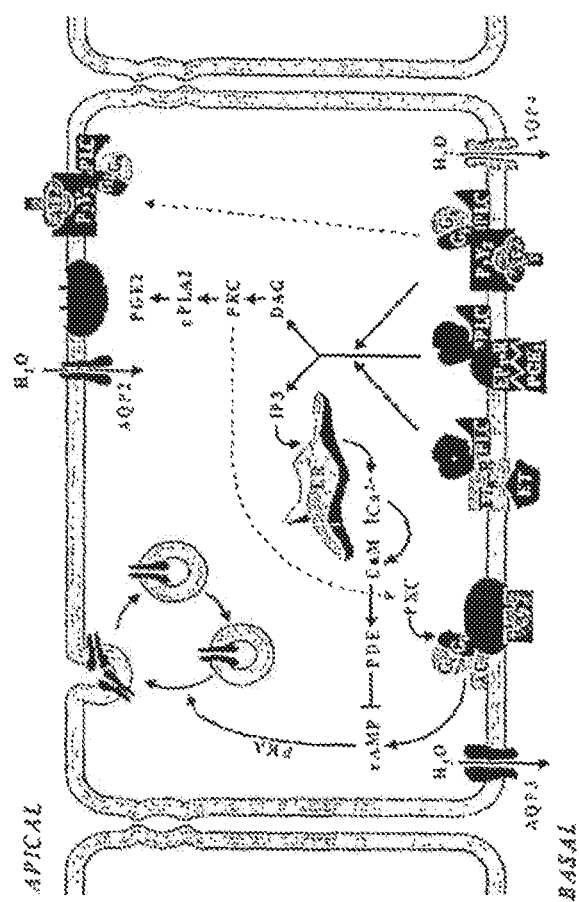
FIG. 2 shows schematic representation of the two mutually opposing signaling pathways and the corresponding membrane receptors involved in the regulation of osmotic water permeability of medullary collecting duct principal cell. The scheme also illustrates the points where the two signaling pathways interact (Schwiebert and Kishore, 2001.

The collecting duct system, which expresses AQP2, AQP3 and AQP4 water channels, accounts for the absorption of 15-20% of the filtered water. This is precisely regulated by AVP, and thus it is crucial for the conservation of body water and excretion of concentrated urine. AQP2 water channel, expressed on the apical plasma membrane and on sub-apical vesicles of collecting duct principal cells, is regulated by AVP. AVP, acting through its V2 receptor a Q protein-coupled receptor, on the collecting duct principal cells, activates membrane bound adenylyl cyclase (AC) to produce cAMP as a second messenger (FIG. 2). The cellular effects of cAMP are believed to be connected to use activation of protein kinase A (PKA), which phosphorylates various, key proteins. AVP has both short- and long-term effects on the collecting duct water permeability. As depicted in FIG. 2, the short-term regulation (in the time frame of few to several minutes) of collecting duct water permeability by AVP involves the translocation of AQP2 water channels from a pool of subapical vesicles to the apical plasma membrane (Nielsen, et al, 1995). The apical plasma membrane is the rate-limiting barrier for the transepithelial water movement, as AQP3, AQP4 are constitutively expressed on the basolateral domain of the collecting duct principal cells under normal conditions (FIG. 2). The long term-regulation (within the time frame of several hours to days) of collecting duct water permeability involves a parallel increase in the absolute amount of AQP2 mRNA and protein (Agre, 2000; Krane and Kishore, 2003). Water deprivation and vasopressin stimulation both increase AQP2 protein expression and apical membrane targeting (Nielsen et al, 1993; DiGiovanni et al, 1994; Kishore et al, 1996). cAMP is capable of stimulating AQP2 gene transcription by acting through CRE and API sites so the AQP2 promoter (Hozawa et al, 1996; Yasui et al, 1997; Matsumura et al, 1997). cAMP activation of AQP2 gene likely occurs by phosphorylation of CREB (CRE binding protein) and the ability of phosphorylated CREB to activate AQP2 gene transcription via binding to CRE sites in the AQP2 promoter. cAMP activation of AQP2 gene could also occur by the induction of c-Fos expression and c-Fos activation of AQP2 transcription via the API site in the AQP2 promoter.

Apart from AVP, a variety of autocrine and paracrine agents, such as PGE2, endothelin and extracellular nucleotides (ATP/UTP), also regulate the collecting duct water permeability. Acting via their respective receptors and the accompanying phosphoinositide signaling pathway these agents decrease the osmotic water permeability of the collecting duct (FIG. 2), even in the presence of AVP (Nadler et al, 1992; Kohan and Hughe, 1993; Kishore et al, 1995; Roman and Lechene, 1981; Rouch and Kudo, 2000). Thus, in the collecting duct, cyclic AMP and phosphoinositide systems are mutually opposing signaling pathways (Teitelbaum, 1992). Diacylglycerol (DAG) formed as a result of stimulation of PI signaling pathway stimulates the activity of PKC, which in turn induces the activity of $G_i$ (inhibitory G protein) associated with the V2 receptor complex. Activation of $G_i$ uncouples the signal for V2 receptor to adenylyl cyclase (AC), resulting in decreased cellular cAMP levels. Activation of PI signaling pathway also results in the stimulation of specific phoshodiesterases (PDEs) through the calcium-caimodulin (CaM) pathway. These PDEs rapidly hydrolyze cAMP and thus reduce the water permeability of the collecting duct as demonstrated in DI+/+ mice, which exhibit constitutively active cAMP-PDE (PDE type IV) (Homma et al, 1991; Frøkiær et al, 1999).

Both in human patients and in laboratory animals, lithium-induced. NDI and post-obstructive uropathy are associated with increased production and excretion of PGE2 in urine. And administration of indomethacin ameliorated these polyuric conditions, indicating that PGE2 is involved in the genesis of polyuria (Lazlo et al, 1980; Fradet et al 1980, 1988; Sugawara et al, 1998). PGE2 is a major prostanoid in the kidney and it interacts with four G protein-coupled E-prostanoid receptors designated EP1, EP2, EP3 and EP4. Through these receptors, PGE2 modulates renal hemodynamics and salt and water excretion (Breyer and Breyer, 2000). PGE2 has an antagonistic effect on AVP-stimulated collecting duct water permeability (Nadler et al, 1992; Han et al, 1994), and molecular mechanisms of this effect of PGE2 on AVP-stimulated water permeability in renal collecting duct have been shown. Using ex-vivo preparations of renal medulla, Zelenina et al (2000) have demonstrated that agonist stimulation of EP3 prostanoid receptor causes retrieval of AQP2 water channels from the apical membrane, thus reducing the abundance of AQP2 protein in the apical membrane, the rate-limiting barrier in the transepithelial water movement in the collecting duct.

P2Y2 receptor is a G protein-coupled nucleotide receptor, linked to phosphoinositide signaling pathway. The agonist potency order of P2Y2 receptor is typically UTP=ATP>ATPγS>2MeS-ATP>α,β-MeATP. Since agonist activation of this receptor results in the mobilization of intracellular $Ca^{2+}$ (Ecelbarger et al., 1994), activation of P2Y2 receptor in medullary collecting duct can result in the downregulation of AVP-stimulated water permeability. Using a model of in vitro microperfused terminal inner medullary collecting duct (IMCD) of rat, it was demonstrated that ATP or UTP, but not ADP (a non-agonist), decreased the AVP-stimulated osmotic water permeability (Pf) in a reversible fashion. Studies using a non-hydrolyzable cAMP analog or forskolin or calphostin C (PKC inhibitor) revealed that the mechanism of this inhibition involves a pre-cAMP formation site, probably the inhibitory G protein (Gi) (Kishore et al., 1995).

In order to establish the molecular expression in IMCD, and to study its regulation in pathophysiological conditions, molecular tools were developed (antibody, primers and cDNA probe) to detect the protein and mRNA of P2Y2 receptor at cellular and tissular levels in the kidney (Kishore et al., 2000a). The rat P2Y2 receptor cDNA cloned from type II alveolar cells, which were used to design an antibody, primers and cDNA probe, has an open reading frame of 1125 base pairs (359-1438 bp) with no introns (Rice et al, 1995). The open reading frame encodes a putative protein of 374 amino acid residues with a predicted molecular weight of 42,275 Daltons in the unglycosylated state (Rice et al, 1995). The protein contains seven transmembrane-spanning domains, characteristic of G protein-coupled receptors. To authenticate the specificity and reliability of the tools, they were also tested on lung tissue, where the expression and function of P2Y2 receptor were well known. RT-PCR and Northern analysis showed expression of P2Y2 mRNA in both lung and kidney. RT-PCR on microdissected collecting duct segments demonstrated P2Y2 receptor mRNA expression in collecting ducts, immunoblots using a C-terminal peptide-derived polyclonal antibody to P2Y2 receptor showed that IMCD expresses two distinct and specific products (47 and 105 kDa), and account for the majority of the receptor expression in the inner medulla. Immunoperoxidase labeling on cryosections showed localization of P2Y2 receptor protein in the apical and basolateral domains of IMCD principal cells in the kidney, and on Clara cells and goblet cells in terminal respiratory bronchioles (Kishore et al, 2000a).

A rise in intracellular calcium, such as the one that occurs following agonist stimulation of P2Y2 receptor, is known to be frequently associated with release of arachidonic acid in several tissues or cells. In most of these tissues or cells, especially those of nonendothelial nature, the predominant prostanoid produced was PGE2. Thus, it was hypothesized that the agonist stimulation of P2Y2 receptor in IMCD should also result in production and release of PGE2. To test this hypothesis, experiments were conducted on freshly prepared rat IMCD fractions, and the effect of activation of P2Y2 receptor on the release of PGE2 was examined. The results show that unstimulated IMCD released significant, amounts of PGE2. Agonist activation of P2Y2 receptor by ATPγS enhanced release of PGE2 from IMCD in a time- and concentration-dependent fashion (FIG. 3). Furthermore, purinergic-stimulated release of PGE2 was completely blocked by non-specific COX inhibitors. Differential COX inhibition studies revealed that purinergic-stimulated release of PGE2 was more sensitive to a COX-1 specific inhibition than COX-2 specific inhibition (Welch, et al. 2003). Because PGE2 is known to affect transport of water, salt, and urea in IMCD (Nadler et al, 1992; Roman and Lechene, 1981; Rouche and Kudo, 2000), the observed interaction of purinergic system with the prostanoid system in IMCD can modulate handling of water, salt, and urea by IMCD and, thus constitutes a complex AVP-independent regulatory mechanism. Thus, the purinergic regulation of medullary collecting duct function extends beyond the direct modulation of AVP-stimulated water permeability.

Potato apyrase (EC 3.6.1.5) is a soluble NTPDase, exhibiting both ATPase and ADPase activities. It is non-toxic and safe to administer either intravenously or intraperitoneally. As documented in FIG. 13, apyrase treatment from day 7 to 14 in lithium-fed rats (i) prevented further increase in the urine flow induced by lithium, and (ii) significantly decreased the P2Y2 receptor-stimulated PGE2 release by IMCD as compared to the apyrase-untreated and lithium-fed rats. Apyrase treatment did not change the urine output or P2Y2-mediated PGE2 release by IMCD in control rats fed with regular diet. These observations showed that apyrase has the ability to decrease the PGE2 formation in acquired NDI by novel means other than the direct inhibition of the activities of cyclooxygenases.

Apyrase can be used for blocking the purinergic signaling, especially following xenograft. Apyrase can also be optimized for administration alone or in combination with specific P2Y2 receptor antagonists to achieve the best possible effect in controlling polyuria and the ensuing hypernatremia.

1. Purinergic Receptors

Several cell membrane receptors, which preferentially bind extracellular nucleotides (ATP/UTP/ADP), and their analogues have been identified, cloned and characterized. There receptors, collectively known as extracellular nucleotide receptors or purinergic receptors have been classified based on their molecular biology, biological actions and pharmacology. Broadly they are divided into P2Y and P2X families. (P1 receptors are not nucleotide receptors; they are adenosine receptors). The P2X receptors are ionotrophic ATP-gates channels that open up to allow small molecules to enter into the cells. Purinergic regulation of renal function encompasses glomerular hemodynamics, microvascular function, tubuloglomerular feedback, tubular transport, renal cell growth and apoptosis for example (Schwiebert and Kishore, 2001; Inscho, 2001).

There are two main families of purine receptors, adenosine or P1 receptors, and P2 receptors, recognizing primarily ATP, ADP, UTP, and UDP (Table 1.) Adenosine/P1 receptors couple to G proteins and have been further subdivided, base on molecular, biochemical, and pharmacological evidence into four subtypes, $A_1$, $A_{2A}$, $A_{2B}$, and $A_3$. In contrast, P2 receptors divide into two families of ligand-gated ion channels and G protein-coupled receptors termed P2X and P2Y receptors, respectively. For example, Table 1 sets forth seven mammalian P2X receptors ($P2X_{1-7}$) and five mammalian P2Y receptors ($P2Y_1$, $P2Y_2$, $P2Y_4$, $P2Y_6$, $P2Y_{11}$) which have been cloned and characterized.

0Table 1: Families of Receptors for Purines and Pyrimidines (Modified from Ralevic V, Burnstock G. Pharmacol Rev 1998 September; 50(3):413-92.)

|  | Adenosine/P1 receptors | P2 receptors | |
| --- | --- | --- | --- |
| Natural ligands | Adenosine | ATP, ADP, UTP, UDP, Adenine dinucleotides | |
| Subgroup | — | P2X | P2Y |
| Type | G protein-coupled | Ion channel Nonselective pore | G protein-coupled |
| Subtypes | $A_1$, $A_{2A}$, $A_{2B}$, $A_3$ | $P2X_{1-7}$, $P2X_n$ | $P2Y_1$, $P2Y_2$, $P2Y_4$, $P2Y_6$, $P2Y_{11}$, $P2Y_{ADP}$ (or $P_{2T}$) Uridine nucleotide-specific |

P2Y receptors are purine and pyrimidine nucleotide receptors that are coupled to G proteins. Most P2Y receptors act via G protein coupling to activate PLC leading to the formation of $IP_3$ and mobilization of intracellular $Ca^{2+}$. Coupling to adenylate cyclase by some P2Y receptors has also been described. The response time of P2Y receptors is longer than that of the rapid responses mediated by P2X receptors because it involves second-messenger systems and down stream mediators mediated by G protein coupling. Five mammalian P2Y receptors ($P2Y_1$, $P2Y_2$, $P2Y_4$, $P2Y_6$, $P2Y_{11}$) have been cloned, and functionally characterized and show distinct pharmacological profiles (Table 2).

TABLE 2

Cloned P2Y receptors

| Receptor | Acession number | cDNA library source | Agonist activity | References |
|---|---|---|---|---|
| P2Y$_1$ (362 amino acids (aa)) | | Human brain | 2MeSATP > ATP ≫ UTP | Schachter et al., 1996 |
| | S81950 | Human prostate and ovary | 2MeSATP > ATP = ADP | Janssens et al., 1996 |
| | Z49205 | Human placenta | | Leon et al., 1995, 1997 |
| | U42030 | Human HEL cells | | Ayyanathan et al., 1996 |
| | X87628 | Bovine endothelium | 2MeSATP = ADP > ATP ≫ ATP | Henderson et al., 1995 |
| | U22830 | Rat insulinoma cells | 2MeSATP > 2Cl-ATP > ATP (α,β-meATP inactive) | Tokuyama et al., 1995 |
| | | Rat ileal myocytes | 2MeSATP = 2ClATP > ADP > ATP (UTP inactive) | Pacaud et al., 1996 |
| | U22829 | Mouse insulinoma cells | | Tokuyama et al., 1995 |
| | U09842 | Turkey brain | 2MeSATP > ADP > ATP; (UTP inactive) | Filtz et al., 1994 |
| | X73268 | Chick brain | 2MeSATP > ATP > ADP; (UTP inactive) | Webb et al., 1993b |
| P2Y$_2$ (373 aa) | U07225 | Human CF/T43 epithelial cells | ATP = UTP ≫ 2MeSATP | Parr et al., 1995 |
| | | Human bone | | Bowler et al., 1995 |
| | | Rat microvascular coronary EC | | Godecke et al., 1996 |
| | U09402 | Rat alveolar type II cells | ATP = UTP | Rice et al., 1995 |
| | L46865 | Rat pituitary | ATP = UTP > ADP = UDP > GTP | Chen et al., 1996b |
| | U56839 | Wistar Kyoto rat[a] | | Seye et al., 1996 |
| | NM_008773 | Mouse NG108-15 neuroblastoma cells | ATP = UTP > ATPγS ≫ 2MeSATP | Lustig et al., 1993 |
| P2y3[b] (328 aa) | X98283 | Chick brain | UDP > UTP > ADP > 2MeSATP > ATP | Webb et al., 1995, 1996a |
| P2Y$_4$ (352 aa) | X91852 | Human placenta | UTP > ATP = ADP[c] | Communi et al., 1996b |
| | | Human placenta | | Stam et al., 1996 |
| | U40223 | Human chromosome X | UTP > UDP (ATP inactive) | Nguyen et al., 1996 |
| | Y14705 | Rat heart | ATP = UTP = ADP = ITP = ATPγS = 2MeSATP = Ap$_4$A > UDP | Bogdanov et al., 1998 |
| P2Y$_6$ (379 aa) | X97058 | Human placenta and spleen | UDP > UTP > ADP > 2MeSATP ≫ ATP | Communi et al., 1996b |
| | NM_057124 | Rat aortic smooth muscle | UTP > ADP = 2MeSATP > ATP | Chang et al., 1995 |
| | U52464 | Activated T-cells | | Southey et al., 1996 |
| P2Y$_{11}$ (371 aa) | 371 | Human placenta | ATP > 2MeSATP ≫≫ ADP; (UTP, UDP inactive) | Communi et al., 1997 |

[a]Tissue not specified.
[b]p2y3 may be the chick homologue of the mammalian P2Y$_6$ receptor.
[c]The reported activity of UDP at the P2Y$_4$ receptor has been shown to be caused by UTP present as a contaminant.
Each of the references herein is incorporated by reference at least for material related to P2Y receptors
Modified from Ralevic V, Burnstock G. Pharmacol Rev 1998 Sep; 50(3): 413-92.

P2Y receptors are 308 to 379 amino acid proteins with a mass of 41 to 53 kDa after glycosylation. A model of the P2Y receptor, based on the primary sequence of the P2Y$_1$ receptor and using the structural homolog rhodopsin as a G protein-coupled receptor template, has identified positively charged amino acid residues in transmembrane regions 3, 6, and 7 that may be involved in ligand binding by electrostatic interactions with the phosphates of ATP (Van Rhee et al., 1995). Several of these amino acids are conserved in other G protein-coupled receptors. Site-directed mutagenesis of the P2Y$_2$ receptor to convert positively charged amino acids in transmembrane regions 6 and 7 to neutral amino acids causes a 100- to 850-fold decrease in the potency of ATP and UTP, which suggests a role for these amino acids in binding purines and pyrimidines (Erb et al., 1995).

TABLE 3

Exemplary P2 receptor signal transduction mechanisms, agonists, and antagonists

| Family | P2X | P2Y |
|---|---|---|
| Receptor type | Ion channel: Nonselective pore[a] | G protein-coupled: $G_{q/11}$, $G_i$[b] |
| Signaling pathway | Not applicable | PLC, AC,[c] $K^+$ channels[d], $PLC_{PC}$,[e] $PLA_2$,[f] PLD,[f] PKC, MAPK[g] |
| Effectors | $Ca^{2+}$ $Na^+ > K^+$ | ↑$IP_3$, ↑$Ca^{2+}$, ↑DAG ↓cAMP[c], $Ca^{2+}$, Cl, $K^+$ currents[h] |
| Nonselective Agonists | ATP[i], ATP□S, 2MeSATP, $Ap_4A$[j] | ATP[i], ATP□S, 2MeSATP, $Ap_4A$[j] |
| P2X/P2Y-selective Agonists | □,□-meATP[l], □,□-meATP[l], BzATP[a] | ADP[c], UTP[m], UTP□S[j], UDP[n], 2Cl-ADP[c], 2MeSADP[c], ADP□S[c], ADP□F[c] |
| Nonselective Antagonists | Suramin, PPADS, Iso-PPADS, P5P, Reactive blue 2, Reactive Red, Trypan Blue, Evans Blue, DIDS | Suramin, PPADS, Iso-PPADS, P5P, Reactive blue 2, Reactive Red, Trypan Blue, Evans Blue, DIDS |
| P2X/P2Y-selective Antagonists | NF023, NF279, KN-62[a] | ARL 67085[o], FPL 66096[o], A3P5PS[k], MRS 2179[k], 2-hexylthio-ATP[p], 2-cyclohexylthio-ATP[p] |

[a]$P2X_7$ and endogenous $P2X_7$-like receptor.
[b]$P2Y_1$ and endogenous $P2Y_1$-like receptors acting through PLC couple to $G_{q/11}$ proteins; $P2Y_1$ and endogenous $P2Y_1$-like receptors acting through adenylate cyclase couple to $G_i$ proteins; $P2Y_2$ and endogenous $P2Y_2$-like receptors, $P2Y_4$ and $P2Y_{ADP}$ receptors couple to $G_{q/11}$ and $G_i$ proteins; p2y3 and $P2Y_6$ receptors couple to $G_{q/11}$ proteins.
[c]$P2Y_1$ and endogenous $P2Y_1$-like receptors and $P2Y_{ADP}$ receptors.
[d]Some endogenous $P2Y_1$-like receptors activate $K^+$ channels via interactions with their G protein subunits.
[e]$P2Y_1$ and endogenous $P2Y_1$-like receptor signaling; possibly downstream of PKC.
[f]$P2Y_1$ and $P2Y_2$ receptors and their endogenous counterparts; signaling possibly downstream of PKC.
[g]$P2Y_1$ and $P2Y_2$ receptors and their endogenous counterparts; signaling downstream of PKC.
[h]Secondary to activation of PLC, although activation of $K^+$ currents by some endogenous $P2Y_1$-like receptors is via direct interactions with G protein subunits.
[i]$P2Y_1$ and $P2Y_2$ receptors and their endogenous counterparts; ATP is an antagonist at $P2Y_{ADP}$ receptors.
[j]$P2Y_2$ and endogenous $P2Y_2$-like receptors.
[k]$P2Y_1$ and endogenous $P2Y_1$-like receptors.
[l]$P2X_1$, $P2X_3$ and heteromeric $P2X_2P2X_3$ receptors.
[m]$P2Y_2$ and endogenous $P2Y_2$-like receptors and $P2Y_4$ receptors.
[n]$P2Y_6$ receptor
[o]$P2Y_{ADP}$.
[p]$P2Y_1$ and endogenous $P2Y_1$-like receptors coupled to AC.

Abbreviations:
AC, adenylate cyclase;
ADP□F, adenosine 5'-O-(2-fluoro)-diphosphate;
ADP□S, adenosine 5'-O-(2-thio-diphosphate);
cAMP, adenosine 3',5'-cyclic monophosphate;
A3P5PS, adenosine 3'-phosphate 5'-phosphosulfate;
ARL 67085, 6-N,N-diethyl-D-□,□-dibromomethylene ATP;
ATP□S, adenosine 5'-O-(3-thiotriphosphate);
BzATP, 3'-O-(4-benzoyl)benzoyl ATP;
DAG, diacylglycerol;
DIDS, 4,4'-diisothio-cyanatostilbene-2,2'-disulfonate;
FPL 66096, 2-propylthio-D-□,□-difluoromethylene ATP;
$IP_3$, inositol 1,4,5-trisphosphate;
KN-62, 1-[N,O-bis(5-isoquinolinesulfonyl)-N-methyl-L-tyrosyl]-4-phenylpiperazine;
Iso-PPADS, pyridoxal phosphate-6-azophenyl-2',5'-disulfonic acid;
MAPK, mitogen-activated protein kinase;
□□-meATP, □□-methylene ATP; □□-meATP, □□-methylene ATP;
2MeSADP, 2-methylthio ADP;
2MeSATP, 2-methylthio ATP;
MRS 2179, $N^6$-methyl modification of 2'-deoxyadenosine 3',5'-bisphosphate;
NF023, symmetrical 3'-urea of 8-(benzamido)naphthalene-1,3,5-trisulfonic acid;
NF279, 8,8'-(carbonylbis(imino-4,1-phenylenecarbonylimino-4,1-phenylenecarbonylimino))bis(1,3,5-naphthalenetrisulfonic acid);
P5P, pyridoxal-5-phosphate;
$PLC_{PC}$, phosphatidylcholine-specific phospholipase C;
PKC, protein kinase C;
$PLA_2$, phospholipase $A_2$;
PLC, phospholipase C;
PLD, phospholipase D;
PPADS, pyridoxal phosphate-6-azophenyl-2',4'-disulfonic acid;
suramin, 8-(3-benzamido-4-methylbenzamido)-naphthalene-1,3,5-trisulfonic acid;
UTPγS, uridine 5'-O-(3-thiotriphosphate).
Modified from Ralevic V, Burnstock G. Pharmacol Rev 1998 Sep; 50(3): 413-92.

Just as P2Y2 agonists inhibit AVP-stimulated osmotic water permeability, so too, antagonists of P2Y receptors can lead to an enhancement of osmotic water permeability. P2Y antagonists, such as those disclosed in Table 3, for example, act at P2Y receptors, and thus can enhance AQP2 presence in the kidney tubule collecting ducts. It is understood that the assays, measurements, and functional limitations, as discussed, herein for agonists are applicable for antagonists as well.

Disclosed are P2Y selective antagonists. Disclosed are P2Y directed antagonists. In certain embodiments, a P2Y directed antagonist is any antagonist that has a greater effect on a P2Y receptor than on a P2X receptor. In other embodiments, P2Y antagonist can be determined by comparing the activity to known selective antagonists, such as those discussed herein. It is understood that the level of activity of each selective antagonist discussed herein, is disclosed. Also disclosed are P2 antagonists that interact with any P2 receptor. It is understood that many P2Y antagonists can be both a selective antagonist as well as a directed antagonists. Also, specifically disclosed are P2Y2 antagonists.

Disclosed herein are methods of treating or modulating diabetes insipidus in a subject, composing administering a composition to the subject, wherein the composition is an antagonist of a P2Y purinergic receptor. In one example, the diabetes insipidus is nephrogenic, however, any form of diabetes insipidus can be treated with the methods disclosed herein. The hallmark of acquired nephrogenic diabetes insipidus is low protein levels of vasopressin-regulated water channel AQP2 in the medullary collecting duct, in the presence of normal of elevated circulating levels of arginine vasopressin (AVP). However, some other forms of NDI are associated with inherited defects in the gene encoding for vasopressin V2 receptor or AQP2 water channel. These conditions are known as inherited NDI. Therefore, any disease that causes low protein levels of vasopressin-regulated water channel in AQP2 in the medullary collecting duct can be treated with the methods disclosed herein.

Increased production of prostaglandin E2 (PGE2) plays a critical role in the genesis of polyuria in diabetes insipidus. It has been demonstrated that there is an accentuated interaction between purinergic and prostanoid systems with markedly enhanced purinergic-mediated PGE2 production and release from the medullary collecting duct in diabetes insipidus. Puringeric system is related to the actions of extracellular nucleotides, which act on the collecting duct via specific P2Y2 receptor. Prostanoids, like PGE2, act on the collecting duct via the EP3 prostanoid receptor. Accentuated interaction between these two systems counteracts the effect of arginine vasopressin, which conserves water and excretes concentrated urine.

Because inhibiting the interaction of the P2Y receptor and prostanoid system can restore normal function to the kidney and ameliorate the symptoms of diabetes insipidus, there are several ways that can be envisioned to treat diabetes insipidus. For example, an antagonist of the P2Y receptor can be used to inhibit the activity of this receptor. Such antagonists can be used alone, or in combination with selective EP3 receptor blockers or low doses of cyclooxygenase inhibitors, or thiazides. In one embodiment described herein, use of the antagonist decreases the level of PGE2. This decrease can be due to a lowered production of PGE2, or due to a reduced amount of release of PGE2 from the medullary collecting duct. In another embodiment, the antagonist can decrease the interaction of the P2Y receptor and the prostanoid system, and PGE2 in particular. Decreasing this interaction can result in less PGE2 being present in the kidney. The antagonist can also work to increase the level of AQP2 in the kidney tubule, which can be due to a decreased amount of PGE2 in the kidney.

Any antagonist of P2Y that inhibits its function can be used with the methods disclosed herein. Examples of such antagonists are disclosed throughout. In one embodiment, the P2Y receptor antagonist is specific of P2Y2. Antagonists such as suramin, reactive blue 2, acid blue 129, acid blue 80, and pyridoxalphosphate-6-azophenyl-2',4'-disulfonic acid (PPADS) can antagonize P2Y2 (Schwiebert and Kishore, 2001). Other P2Y2 antagonists can be identified by methods described herein.

Also disclosed herein are combination therapies to be used together with a P2Y-antagonist. Any of the combination therapies described herein can be used singly with the P2Y antagonist, or in combination with each other as well as the P2Y antagonist.

For example, apyrase or other nucleotide hydrolyzing enzymes, such as NTPDases (nucleoside triphosphate diphosphohydrolases) can be used with the methods disclosed herein, either alone or in combination with specific P2Y2 receptor antagonists to achieve the best possible effect in controlling polyuria and hypernatremia.

Disclosed herein are methods wherein the P2Y antagonist is used in combination with inhibitors of prostaglandin synthesis. Inhibitors of prostaglandin synthesis, such as indomethacin (non-specific) and specific inhibitors of cyclooxygenase-1 (COX-1) and COX-2 (eg. rofecoxib), for example, have previously been used in the treatment of NDI. The dose of inhibitors of prostaglandin synthesis can be reduced by combining them with a P2Y2 receptor antagonist. More than one inhibitor of prostaglandin synthesis can be used with the P2Y antagonist.

Also disclosed are methods wherein the P2Y antagonist is used in combination with inhibitors of arachidonic acid release. Since the availability of "free" arachidonic acid is the rate-limiting factor in the synthesis of prostaglandins by COX, agents that reduce the availability of "free" arachidonic acid can also limit the synthesis of prostaglandins such as PGE2. Examples of such agents are those that inhibit phospholipases such as cytosolic phospholipase A2 (cPLA2), calcium insensitive phospholipase A2 (iPLA2), and phospholipase D (PLD), for example. An agent that decreases the availability of free arachidonic acid and an antagonist of P2Y receptor can be combined. More than one inhibitor of arachidonic acid release can be used in combination with a P2Y antagonist.

Disclosed herein are methods wherein a P2Y antagonist is used in combination with a composition that increases cAMP. Furthermore, since cellular cyclic AMP are critical for the expression of AQP2 water channel, combination therapies can be used wherein agents that increase cellular cAMP are used in combination with a P2Y antagonist. These include, but are not limited to, inhibitors of phosphodiesterases (PDEs) a group of enzymes that hydrolyze cAMP. Inhibitors of PDEs increase the cellular cAMP levels by preventing its degradation. In another example, the cellular cAMP levels can be increased by activating adenylyl cyclase (AC), the enzyme(s) that produce cAMP from ATP. One such agent is Forskolin. Hence, included in the methods disclosed herein are combination therapies that include agents which increase cellular cAMP either by preventing its degradation (inhibitors of PDEs) or increase its synthesis (activators of AC, such as Forskolin). Since increased cellular cAMP acting through protein, kinase A (PKA) caused shuttling of AQP2 to apical membrane, a combination therapy including PKA activator and P2Y2 receptor antagonist can also be used.

Also disclosed are methods wherein a P2Y antagonist is used in combination with a composition that inhibits protein kinase C (PKC). PKC plays a critical role in the P2Y2 receptor-mediated decrease in water transport in the collecting duct. Hence a combination therapy including P2Y receptor antagonist and an inhibitor of PKC can be used with the methods described herein. Similarly, MAP kinases play critical role in the activation of some phospholipases. Hence a combination therapy including a MAP kinase kinase (MEK) inhibitor and a P2Y2 receptor antagonist can also be used with the methods disclosed herein.

The methods disclosed heroin also comprise a P2Y antagonist used in combination with a diuretic. Since polyuria of NDI can be ameliorated by dosing of a thiazide with a potassium, sparing diuretic like amiloride, combination therapies including either a diuretic or amiloride or both along with a P2Y receptor antagonist can be used with the method disclosed herein. Also, combinations of thiazide with or without amiloride and prostangladin synthesis inhibitors given along with P2Y2 receptor antagonists can be used with the methods disclosed herein.

Also disclosed are methods wherein thiazide is used in combination with a prostaglandin synthesis inhibitor. The P2Y antagonist can be used in combination with a non-specific blocker of prostanoid receptors or with a selective blocker of prostanoid receptors. The selective blocker can involve an EP3 prostanoid receptor, or a combination of EP3 and EP1 prostanoid receptors, or any one or more other prostanoid receptors.

Also disclosed are methods wherein the P2Y antagonist is used m combination with a non-specific or specific blockers of prostaglandin transporters (PGT). Prostaglandin transporters (PGT) are specific membrane proteins that facilitate the "rapid" release of prostaglandins from cells. (Prostaglandins, being lipid derivatives, can diffuse through cell membranes even without PGTs, albeit at a lesser rapidity). The release of PGE2 from cells, including collecting duct principal cells, is dependent on specific PGTs in the cell membranes (Bao et al, 2002). Several PGTs have been cloned and characterized. These are broadly expressed in COX-positive cells and are coordinately regulated by COX. However, in Madin-Darby canine kidney cells (MDCK cells), it appears that the PGTs are exocytotically inserted into the apical membrane, where they control the concentration of luminal prostglandins (Endo et al, 2002. Therefore, the P2Y antagonist can be used in combination with an agent that inhibits or blocks the release of prostaglandins from cells. Alternatively, the P2Y receptor antagonist can be used in combination with agents that enhance the degradation or inactivation of prostaglandins release from the cells.

Also disclosed herein are P2Y agonists, as well as methods for treating fluid retention by administering a P2Y agonist. For example, agonists of P2Y2 receptor act as mild diuretics acting on the medullary collecting duct. The currently available diuretic agents act on either the medullary thick ascending limb (loop diuretics such as furosemide) or on the distal nephron (thiazide diuretics). These two classes of diuretics inhibit the water reabsorption by essentially interfering with salt absorption. Because, of this, their clinical usage has to be carefully monitored, failing which patients may suffer sodium and other electrolyte imbalances. However, in the medullary collecting duct the absorption of water is not linked to the absorption of salt (free water absorption). Hence targeting the medullary collecting duct for diuretic action, using P2Y2 receptor agonists can provide better diuretic action without the associated complications of electrolyte imbalances. Therefore, disclosed herein are methods of administering to a subject a P2Y agonist, wherein the P2Y agonist acts as a diuretic.

Diuretics are useful in the treatment of various medical disorders which result in fluid retention, congestive heart failure, and hypertension. As such these pharmaceutical compounds can be useful in treating the fluid retention and dilutional hyponatremia associated with a number of severe pathologies such as congestive heart failure, chronic liver disease, hepato-renal syndrome, benign and malignant tumors of the lung, liver and central nervous system. Because diuretics are useful in such a large variety of disorders, their use is widespread but complicated by an associated loss of electrolytes systems functions.

In therapeutic use for treating, or combatting, water retentive states in warm-blooded animals, the compounds or pharmaceutical compositions there of can be administered orally and/or parenterally at a dosage to obtain and maintain a concentration, that is, an amount, or blood-level of active component in the animal undergoing treatment which will be effective as a diuretic. Generally, such diuretic effective dosage of active component will be in the range of about 0.15 to about 30, more preferably about 1 to about 10 mg/kg of body weight/day. It is to be understood that the dosages may vary depending upon the requirements of the patient, the severity of the water retention being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four time per day.

2. General Composition Information

Disclosed herein are many types of compositions, including the P2Y antagonists, as well as PGE2, AQP2, arginine vasopressin, and the P2Y receptors. The information contained herein relates to all of these compositions, as well as analogs, fragments, and portions thereof.

a) Nucleic Acids

There a variety of molecules disclosed herein that are nucleic acid based, including for example the nucleic acids that encode, for example the purinergic receptors, as well as various functional nucleic acids. The disclosed nucleic acids are made up of, for example, nucleotides, nucleotide analogs, nucleotide substitutes. Non-limiting examples of these and other molecules are discussed herein. It is understood that for example, when a receptor is expressed in a cell that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

(1) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage, the base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of nucleotide would be 3'-AMP (3'-adenosine menophosphate) or 5'-GMP (5'-guanosine monophosphate).

A nucleotide analog is a nucleotide, which contains some type of modification to the base, sugar, or phosphate moieties. Modifications to nucleotides are well know in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

(2) Nucleotides and Related Molecules

A nucleotide analog is a nucleotide, which contains some type of modification to the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808. Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993, Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the Mowing modifications at the 2' position: OH; F; O-, S-, or N-alkyl; O-, S-, or N-alkenyl; O-, S- or N-alkynyl; or O-alkyl-O-alkyl wherein the alkyl, alkenyl and alkynyl can be substituted or unsubstituted $C_1$ to $C_{10}$, alkyl or $C_2$ to $C_{10}$ alkenyl and alkynyl. 2' sugar modifications also include but are not limited, to —O[(CH$_2$)$_n$O]$_m$ CH$_3$, —O(CH$_2$)$_n$ OCH$_3$, —O(CH$_2$)$_n$ NH$_2$, —O(CH$_2$)$_n$ CH$_3$, —O(CH$_2$)$_n$—ONH$_2$, and —O(CH$_2$)$_n$ON [(CH$_2$)$_n$CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications can also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs can also have sugar mimetics such as cyclobutyl moieties in place of the pentofuranosyl sugar. There are numerous United States patents that teach the propagation of such modified sugar structures such as U.S. Pat. Nos. 4,981,957; 5,118,800; 5,319,080; 5,359,044; 5,393,878; 5,446,132; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modeled phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleosides containing modified phosphates and include but are not limited to, U.S. Pat. Nos. 3,687,808, 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821;

5,545,306; 5,550,111; 5,563,253; 5,571,799; 5,587,361; and 5,625,050, each of winch is herein incorporated by reference.

It is understood that nucleotide analogs need only contain a single modification, but can also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones, formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous Unites States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 4,589,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine (PNA). U.S. Pat. Nos. 5,539,082; 5,714,331; and 5,719,262 teach how to make and use PNA molecules, each of which is herein incorporated by reference. (See also Nielsen et al., Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci. 1992, 660, 106-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,514,077; 5,486,603; 5,512,439; 5,578,718; 5,608,046; 4,587,044; 4,605,735; 4,667,025; 4,792,779; 4,789,737; 4,824,941; 4,835,263; 4,876,335; 4,904,582; 4,958,013; 5,082,830; 5,112,963; 5,214,136; 5,082,830; 5,112,963; 5,214,130; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

(3) Sequences

There are a variety of sequences related to the purinergic receptors having the following Genbank Accession Numbers and these sequences and others are herein incorporated by reference in their entireties as well as for individual subsequences contained therein.

There are many sequences of the P2Y receptor, and specifically the P2Y2 receptor, which can be found for example in Genbank Accession Nos: AY620400, AY0662405, AY620399, NM001004501, NM183168, for example, all of which are herein incorporated by reference. It is understood that the description related to this sequence is applicable to any sequence related to purinergic receptors, for example, unless specifically indicated otherwise. Those of skill in the art understand how to resolve sequence discrepancies and differences and to adjust the compositions and methods relating to a particular sequence to other related sequences. Primers and/or probes can be designed for any of the purinergic receptor sequences given the information disclosed herein and known in the art.

(4) Primers and Probes

Disclosed are compositions including primers and probes, which are capable of interacting with the purinergic receptors as disclosed herein. In certain embodiments the primers are used to support DNA amplification reactions. Typically the primers will be capable of being extended in a sequence specific manner. Extension of a primer in a science specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the printer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primes in a sequence specific manner. Typically the disclosed primers hybridize with a purinergic receptor nucleic acid or region of the purinergic receptor nucleic acid or they hybridize with the complement off the purinergic receptor nucleic acid or complement of a region of the purinergic receptor nucleic acid.

b) Delivery of the Compositions to Cells (1) Nucleic Acid Delivery

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transaction, including viral vectors, chemical transfectants, or physicomechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

In the methods described herein, which include the administration and uptake of exogenous DNA into the cells of a subject (i.e., gene transduction or transfection), the disclosed nucleic acids can be in the form of naked DNA or RNA, or the nucleic acids can be in a vector for delivering the nucleic acids to the cells, whereby the encoding DNA or DNA or fragment is under the transcriptional regulation of a promoter, as would be well understood by one of ordinary skill in the art as well as enhancers. The vector can be a commercially available preparation, such as an adenovirus vector (Quantum Biotechnologies, Inc. (Laval, Quebec, Canada).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic add encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5; 941-948, 1994), adeno-associated viral (AAV) vectors (Goodman, et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). The disclosed compositions and methods can be used in conjunction with any of these or other commonly used gene transfer methods.

As one example, if the antibody-encoding nucleic acid or some other nucleic acid encoding a purinergic receptor interactions is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six-month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated Into the host genome.

Other general techniques for integration into the host genome include, for example systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

(2) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed compositions or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci. USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md., SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector can be delivered in vivo by electroporation, the technology for which is available from Genetronics, Inc. (San. Diego, Calif.) as well as by means of a SONOPORATION machine (ImaRx Pharmaceutical Corp., Tucson, Ariz.).

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992), Pietersz and McKenzie, *Immunolog. Reviews,* 129: 57-80, (1992); and Roffler, et al., *Biochem. Pharmacol,* 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al. *Cancer Research* 49:6214-6220, (1989); and Litzinger and Huang, *Biochimica et Biophysica Acta,* 1104: 179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, *DNA and Cell Biology* 10:6, 399-409 (1991)).

(3) In Vivo/Ex Vivo

As described above, the compositions can be administered in a pharmaceutically acceptable carrier and can be delivered to the subjects cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

c) Expression Systems

The nucleic acids that are delivered to cells typically contain expression-controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

(1) Viral Promoters and Enhancers

Preferred promoters controlling transcription from vectors in mammalian host cells can be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113(1978)). The immediate early promoter of the human cytomegalovirus is conveniently obtained as a HindIII E restriction fragment (Greenway, P. J. et al., *Gene* 18: 355-360) (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol, Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer can be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression sectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites, it is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. it is also preferred that the transcribed units contain other standard sequences alone or in combination with the above sequences improve expression from, or stability of, the construct.

(2) Markers

The vectors can include nucleic acid sequence encoding a marker product. This marker product is used to determine if the gene has been delivered to the cell and once delivered is being expressed. Preferred marker genes are the E. Coli lacZ gene, which encodes β-galactasidase, and green fluorescent protein.

In some embodiments the marker can be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells, and mouse LTK-cells.

These cells lack the ability to grow without the addition of such nutrients as thymidine or hypoxanthine. Because these cells lack certain genes necessary lot a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209; 1422 (1980) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

d) Peptides (1) Protein Variants

As discussed herein, there are numerous variants of the purinergic receptor proteins and that are known and herein contemplated. In addition, to the known functional purinergic receptor species variants there are derivatives of the purinergic receptor proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 4 and 5 and are referred to as conservative substitutions.

TABLE 4

Amino Acid Abbreviations

| Amino Acid | Abbreviations | |
|---|---|---|
| alanine | Ala | A |
| allosoleucine | AIle | |
| arginine | Arg | R |
| asparagine | Asn | N |
| aspartic acid | Asp | D |
| cysteine | Cys | C |
| glutamic acid | Glu | E |
| glutamine | Gln | Q |
| glycine | Gly | G |
| histidine | His | H |
| isolelucine | Ile | I |
| leucine | Leu | L |
| lysine | Lys | K |
| phenylalanine | Phe | F |
| proline | Pro | P |
| pyroglutamic acid | pGlu | |
| serine | Ser | S |
| threonine | Thr | T |
| tyrosine | Tyr | Y |
| tryptophan | Trp | W |
| valine | Val | V |

TABLE 5

Amino Acid Substitutions

| Original Residue | Exemplary Conservative Substitutions, others are known in the art. |
|---|---|
| Ala | ser |
| Arg | lys, gln |
| Asn | gln; his |
| Asp | glu |
| Cys | ser |
| Gln | asn, lys |
| Glu | asp |
| Gly | ala |
| His | asn; gln |
| Ile | leu; val |
| Leu | ile; val |
| Lys | arg; gln; |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 5, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some distances, amidation of the C-terminal carboxyl.

It is understood that one way to define the variants and derivatives of the disclosed proteins herein is through defining the variants and derivatives in terms of homology/identity so specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988) by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M.

Science 244:48-52, 1989, Jaeger et al. *Proc. Natl. Acad. Sci. USA* 86:7706-7710, 1989, Jaeger et al, *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence cannot be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular organism from which that protein arises is also known and herein disclosed and described.

e) Pharmaceutical Carriers/Delivery of Pharmaceutical Products

As described herein, the compositions, such as the P2Y2 antagonists, can also be administered in vivo is a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions can be administered orally, parenterally (e.g., intravenously), by intramuscular injection, by intraperitoneal injection, transdermally, extracorporeal, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the composition. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, it used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration type of ligand, ligand valency, and ligand concentration. Molecular and cellular mechanisms of receptor-mediated endocytosis have been reviewed (Brown and Greene, *DNA and Cell Biology* 10:6, 399-409 (1991)).

(1) Pharmaceutically Acceptable Carriers

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antagonist which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface-active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment, is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antagonists can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids or binders can be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such, as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

(2) Therapeutic Uses

Effective dosages and schedules for administering the compositions can be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antagonist can be found in the literature on therapeutic uses of antibodies, e.g., Handbook of Monoclonal Antibodies, Ferrone et al., eds., Noges Publications, Park Ridge, N.J., (1985) ch, 22 and pp. 303-357; Smith et al., Antibodies in Human Diagnosis and Therapy, Haber et al., eds., Raven Press, New York (1977) pp. 365-389. A typical daily dosage of the P2Y2 antagonist used alone might range from about 1 µg/kg to up to 100 mg/kg of body weight or more per day, depending on the factors mentioned above.

Following administration of a disclosed composition, such as a P2Y antagonist, for the treatment of diabetes insipidus, the efficacy of the therapeutic composition can be assessed in various ways well known to the skilled practitioner. For instance, one of ordinary skill in the art will understand that the compositions disclosed herein are efficacious in modulating, such as reducing PGE2 in the kidney, by observing that the composition reduces PGE2. PGE2 can be measured by methods that are known in the art.

The compositions described herein can be used alone or in combination with other therapies as disclosed herein.

The compositions disclosed herein, specifically P2Y agonists, can be used as a diuretic.

The compositions that modulate PGE2 can be administered prophylactically to patients or subjects who are at risk for acquiring diabetes insipidus.

f) Computer Readable Mediums

It is understood that the disclosed nucleic acids and proteins and compositions can be represented as a sequence consisting of the nucleotides or amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences and ATP or ATP analogs on computer readable mediums, such as, commercially available floppy disks, tapes, chips, hard drives, compact disks, and videodisks, or other computer readable mediums. Also disclosed are the binary code representations of the disclosed sequences and ATP or ATP analogs. Those of skill in the art understand what computer readable mediums. Thus, computer readable mediums on which the nucleic acids or protein sequences are recorded, stored, or saved are also disclosed.

g) Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein. Disclosed are chips where at least one address is the composition, such as a P2Y2 antagonist, disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

h) Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include a P2Y2 antagonist in a formulation for delivery to a subject with NDI.

C. Methods of Making the Compositions

The compositions disclosed herein and the compositions necessary to perform the disclosed methods can be made using any method known to those of skill in the art for that particular reagent or compound unless otherwise specifically noted.

D. Methods of Screening

Disclosed are methods of identifying art antagonist of P2Y2 receptors comprising the steps of contacting a kidney cell with an agent to be tested and detecting a decrease in PGE2. A decrease in PGE2 indicates a P2Y2 antagonist.

Also disclosed are methods of identifying an antagonist of P2Y2 receptors comprising the steps of contacting a kidney cell with an agent to be tested and detecting an increase in AQP2 in the kidney collecting ducts. An increase in AQP2 indicates a P2Y antagonist.

Also disclosed are methods of screening for an antagonist of P2Y2, comprising contacting a kidney cell with a test compound; detecting PGE2 levels in the kidney cell; and screening for a sustained reduction in PGE2 as compared to a control level, indicating an antagonist of P2Y2.

Also disclosed are methods of screening for an antagonist of P2Y2, comprising contacting a kidney cell with a test compound; detecting AQP2 levels m the kidney tubule collecting ducts; and screening for a sustained increase in AQP2 levels as compared to a control level, indicating an antagonist of P2Y2.

The screening methods disclosed herein can take place in the presence of arginine vasopressin (AVP). The collecting duct system is precisely regulated by AVP, and thus it is crucial for the conservation of body water and excretion of concentrated urine. AQP2 water channel, expressed on the apical plasma membrane and on sub-apical vesicles of collecting duct principal cells, is regulated by AVP. AVP, acting through its V2 receptor, a G protein-coupled receptor, on the collecting duct principal cells, activates membrane bound adenylyl cyclase (AC) to produce cAMP as a second messenger (FIG. 2). Therefore, cAMP can also be measured in the screening claims described herein.

Also disclosed are methods of identifying an antagonist of P2Y2 receptors comprising the steps of contacting a kidney cell with an agent to be tested and detecting an increase in intracellular calcium. An decrease in intracellular calcium indicates a P2Y2 antagonist.

Screening can take place in multi-well plates. Multi-well plates are standard in the art and come in a variety of sizes and shapes. For example, the multi-well plate can be 24, 48, or 96 well plates. Such screening assays can be automated or further modified for high throughput analysis. For high throughput screening, each well can include numerous test components. If a positive reaction is detected in a well, the screening is repeated with one of the test compounds contained in a single well.

The invention also provides methods of screening for P2Y2 receptor antagonist, comprising contacting a first kidney cell with more than one test compound, detecting PGE2 levels in the first kidney cell; selecting each of test compounds in the group that contacted the first kidney cell, wherein the first kidney cell showed a sustained decrease in PGE2, contacting a second kidney cell with one test compound from the step of selecting each of the test compounds; and detecting PGE2 levels in the second kidney cell, a sustained decrease in PGE2 as compared to a control level, indicating a P2Y2 antagonist.

The invention also provides methods of screening for a P2Y2 receptor antagonist, comprising contacting a first kidney cell with more than one test compound; detecting AQP2 in the kidney tubules of the first kidney cell; selecting each of test compounds in the group that contacted the first kidney cell, wherein the first kidney cell showed a sustained increase in AQP2 in the kidney tubules; contacting a second kidney cell with one test compound front the step of selecting each of the test compounds; and detecting AQP2 levels in the kidney tubules of the second kidney cell, a sustained increase in AQP2 levels in the kidney tubules as compared to a control level, indicating a P2Y2 antagonist.

Also contemplated are agents identified by the screening methods described herein, as well as methods of making those agents. An example of a method of making an agent includes identifying the agent using the methods provided herein, and manufacturing the agent or manufacturing the agent in a pharmaceutically acceptable carrier.

Also provided are methods of screening for a P2Y2 antagonist, comprising contacting a test compound with a cell that expresses a heterologous nucleic acid that encodes a P2Y2 receptor; and detecting PGE2 levels in the cell; a sustained reduction in PGE2 as compared to a control level, indicating a P2Y2 antagonist. Preferably, the cell is a cell that lacks the receptor prior to introduction of the heterologous nucleic acid. The cell can be transiently transfected with the heterologous nucleic acid.

By "heterologous nucleic acid" is meant that any heterologous or exogenous nucleic acid can be inserted into a vector for transfer into a cell, tissue or organism. The nucleic acid can encode a polypeptide or protein or an antisense RNA, for example. The nucleic acid can be functionally linked to a promoter. By "functionally linked" is meant such that the promoter can promote expression of the heterologous nucleic acid, as is know in the art, such as appropriate orientation of the promoter relative to the heterologous nucleic acid. Furthermore, the heterologous nucleic acid preferably has all appropriate sequences for expression of the nucleic acid, as known in the art, to functionally encode, i.e., allow the nucleic acid to be expressed. The nucleic acid can include, for example, expression control sequences, such as an enhancer, and necessary information processing sites, such as ribosome binding sites, RNA splice sites, polyadenylation sites, and transcriptional terminator sequences.

The heterologous nucleic acid introduced into the cell can include, for example, one or more nucleic acids encoding one or more subparts of the receptor. For example, four different subparts of a P2Y receptor could be encoded in four different nucleic acids or in three, two, or one nucleic acids. In various embodiments, specific antagonists can be tested using different subparts for the channel. These assays would thus identify antagonists for different subtypes of P2Y channels (e.g., P2Y1, P2Y2, etc.) that complex together to form the fully functional receptor channel present in native kidney cells.

Also provided are methods of screening for an P2Y2 antagonist, further comprising screening for reversibility of response by removing the antagonist during the assay and testing PGE2 levels after the antagonist is removed. In one embodiment, the antagonist identified by the methods described herein is a reversible antagonist.

Optionally, the compound being screened can augment the effects of other compounds such as ATP, zinc, or ionomycin, for example. In this case, the compound being screened can be tested in the presence of another compound that stimulates the receptor. For example, the kidney cell can be in a solution containing an effective amount of ATP. An "effective amount of ATP" is defined as about 1 to about 500 mM of ATP or 10 to about 200 mM of ATP.

The above is generally applicable for measuring PGE2 levels whether by fluorescence, luminescent or other detection techniques. The invention has particular application to high throughput screening and whole cell functional assays for compounds with biological activity. In the most general promise, one can use any type of compound that can affect the P2Y2 receptor.

The process is also applicable for screening compounds with biological activity characterized by rapid and transient changes in PGE2. Examples include the evaluation of receptor antagonists that elicit changes in cellular PGE2 levels.

Glow luminescence assays have been readily adopted into high throughput screening facilities because of their intrinsically high sensitivities and long-lived signals. The signals for chemiluminescence systems such as luciferase and beta-galactosidase reporter genes or for alkaline phosphatase conjugates are often stable for several hours.

Several commercial luminescence and fluorescence detectors are available that can simultaneously inject liquid into single or multiple wells such as the WALLAC VICTOR2 (single well, MICROBETA® JET (six wells), or AURORA VIPR (eight wells). Typically, these instruments require 12 to 96 minutes to read a 96-well plate in flash luminescence or fluorescence mode (1 min/well). An alternative method is to inject the inhibitor/antagonist into all sample wells at the same time and measure the luminescence in the whole plate by imaging with a CCD camera, similar to the way that calcium responses are read by calcium-sensitive fluorescent dyes in the FLIPR or FLIPR-384 instruments. Other luminescence or fluorescence imaging systems include LEADSEEKER from AMERSHAM, the WALLAC VIEWLUX™ ultraHTS microplate imager, and the MOLECULAR DEVICES CLIPR imager.

PE BIOSYSTEMS TROPIX produces a CCD-based luminometer, the NORTHSTAR™ HTS Workstation. This instrument is able to rapidly dispense liquid into 96-well or 384-well microtiter plates by an external 8 or 16-head dispenser and then can quickly transfer the plate to a CCD camera that images the whole plate. The total time for dispensing liquid into a plate and transferring it into the reader is about 10 seconds.

E. Examples

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Altered P2Y2 Receptor Protein Abundance in Inner Medulae, and Purinergic-Mediated PGE2 Release from IMCD Under Conditions of Hydration and Dehydration In rats subjected to water loading or hydration, the urine osmolality and circulating levels of AVP are very low, similar to the condition of compulsive water drinking seen in humans. This is associated with a decreased protein abundance and altered subcellular localization of AVP-regulated water channel AQP2 in inner medulla. Conversely, water deprivation or thirsting results in elevated urine osmolality and circulating levels of AVP, and is associated with an increased protein abundance and apical membrane targeting of AQP2 in inner medulla (Terris et al, 1996). It was observed that expression and activity of P2Y2 receptor are markedly altered in inner medullae under conditions of hydration and dehydration (FIG. 4).

Specifically, the data show that the expression of P2Y2 receptor protein in inner medulla is affected by the hydration status of the animals, with hydrated polyuric rats showing significantly higher levels of protein as compared to dehydrated oliguric rats. The changes in P2Y2 receptor protein are paralleled by similar changes in its mRNA expression as determined by real-time RT-PCR. Furthermore, observations (Sun et al, 2004) show that when challenged with ATPγS, a non-hydrolyzable agonist of P2Y2 receptor, freshly isolated IMCD from dehydrated rats showed <10% increase in PGE2 production and release, as compared in a ~160% increase seen in hydrated rats. The corresponding increase in IMCD of control rats was ~37% (FIG. 4, panel E). These observations are paralleled by urinary excretion of PGE2 metabolite, which was very low in dehydrated (11% of controls) and high in hydrated (153% of controls) rats (FIG. 4, panel D). Thus, the data clearly establish accentuated interactions between purinergic and prostanoid systems in IMCD in hydrated polyuric condition. This constitutes a novel AVP-independent regulatory mechanism of medullary collecting duct function, which plays an important role in pathophysiological conditions as well.

Figure 6:
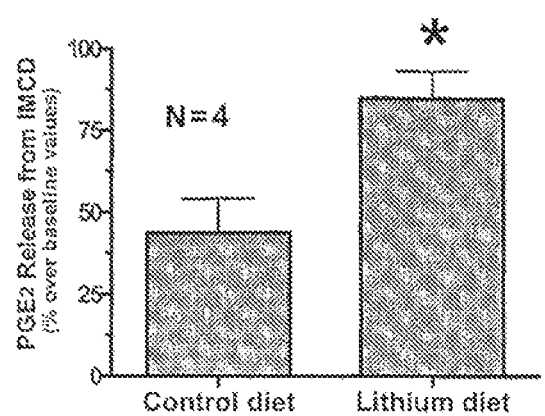
FIG. 6 shows protein abundance and mRNA expression of P2Y2 receptor in inner medulla (panel A & B), and in vitro IMCD response to purinergic-stimulated PGE2 release (panel C) in rats fed control or lithium-added diets for 21 days. Inner medullae from control or lithium diet fed rats were pooled separately, and fractions enriched in IMCD were prepared from these pools by collagenase and hyaluronidase digestion. Experiments were carried out as described for hydrated and dehydrated rats in FIG. 4, ATP.gamma.S-stimulated release of PGE2 in each group was computed as percent increase over the respective vehicle controls (baseline values). The mean increase in P2Y2-stimulated release of PGE2 in lithium group is .about.2-fold higher as compared to the mean increase in controls. Results are expressed as mean.+−.SEM, *significantly different from the control group.
Figure 8A:
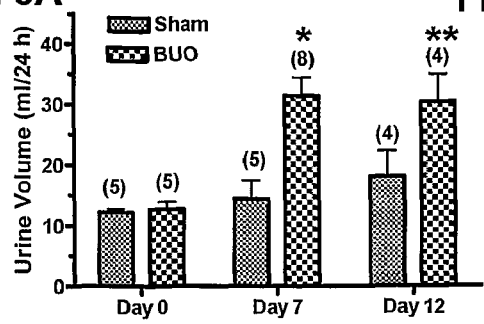
FIGS. 8A, 8B, 8C, 8D, 8E, and 8F show the characterization of rat model of NDI induced by bilateral ureteral obstruction (BUO) and release. Panel A: Twenty-four hour urine volumes in sham operated and BUO rats. *significantly different from the corresponding sham operated values by ANOVA followed by Tukey-Kramer Multiple Comparison Test; **significantly different from the corresponding sham operated values by unpaired t test. Panel B: Urine osmolalities in sham operated and BUO rats. *significantly different from the corresponding sham operated values. The decrease in mean urine osmolality in BUO rats on day 12 did not attain statistical significance (P=0.112) due to the large variation in sham operated rats and small sample size. Panel C: Water intake in sham operated rats (pooled values from day 0, 7 and 12) and BUO rats at day 0, 7 and 12. *significantly different from the values in BUO day 0 and sham operated groups. Panel D: Urinary excretion of PGE2 metabolite in sham operated and BUO rats measured on day 12 urine samples. *significantly different from the sham operated values. Panel E: Protein abundance of AQP2 water channel in the inner medulla of sham operated and BUO rats euthanized on day 12. Panel F: Densitometry of AQP2 protein hands in sham operated and BUO rats. *significantly different from the corresponding band density in sham operated group. Results are expressed as mean.+−.SEM. The number in parenthesis indicates the number of animals examined. Since the surgical procedures were performed on small batches of animals on each time, some of the urine samples could not be collected for analysis. Day 0 represents the period just prior to the first surgical operation performed to obstruct the ureters.
Figure 8B:
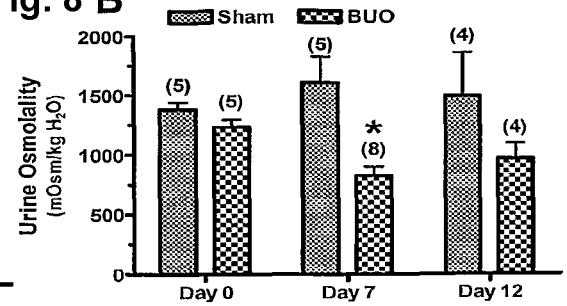
Figure 8C:
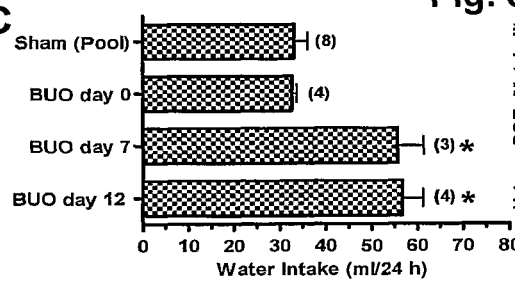
Figure 8D:
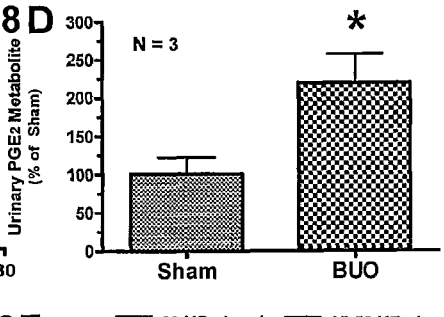
Figure 8E:
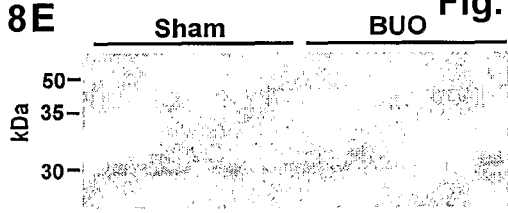
Figure 8F:
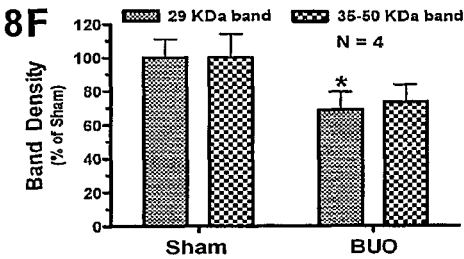
Figure 11:
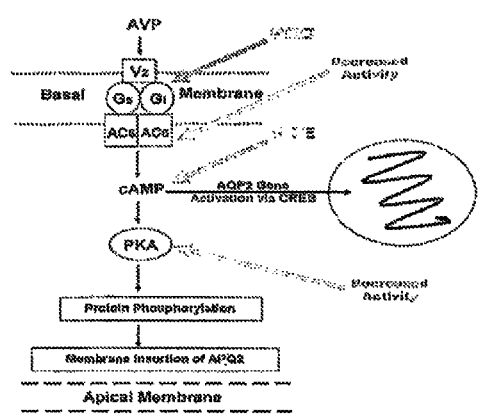
FIG. 11 shows the sequence of intracellular events leading from vasopressin V2 receptor on the basolateral membrane to the insertion of AQP2 water channels into the apical membrane of collecting duct principal cell. The potential pre-cAMP formation sites that can be disrupted are (i) activation of inhibitory G protein (Gi) by the increased activity of PKC brought about by diacylglycerol (DAG) formed as a result of stimulation of the PI signaling pathway by various autocrine and paracrine agents (PGE2, ATP/UTP or endothelin), and (ii) decreased activity of adenylyl cyclase (AC) isoforms 5 and 6 expressed so the medullary collecting duct. The potential post-cAMP formation sites which can be disrupted are (i) rapid hydrolysis of cAMP by phoshodiesteases (isofoms III and IV) expressed in medullary collecting duct, and (ii) decreased activity of PKA, resulting in decreased protein phosphorylation and membrane insertion of AQP2.

2. Example 2: Purinergic and Prostanoid Interactions in Lithium-Induced Nephrogenic Diabetes Insipidus Groups of male Sprague-Dawley rats (N=8 per group) were fed with either a standard rat chow or standard rat chow with added lithium chloride (40 mmol/kg; custom prepared by MP Biomedicals, Aurora, Ohio) for 21 days. Urinary output and water intake were monitored periodically. Rats were euthanized on day 21, and kidney tissue and blood were collected and processed for molecular and functional studies and serum lithium levels, respectively. The mean (±SEM) lithium level in the blood of rats on lithium diet was 1.18±0.05 mmol/L (N=8), which is within the therapeutic range seen in patients on lithium therapy (0.5 to 1.5 mmol/L). Thus this model mimics the clinical condition of lithium therapy, and does not result in overt lithium toxicity. FIG. 5 depicts the characterization of the lithium model with respect to body weight, water intake, urine parameters and protein abundance of AQP2 water channel in inner medulla. FIG. 6 shows the protein abundance and mRNA expression of P2Y2 receptor in inner medulla, and purinergic-mediated PGE2 release from IMCD of control and lithium diet fed rats. FIG. 7 shows the mRNA expression of cytosolic phospholipase (cPLA2), the major phospholipase in the kidney for the release of arachidonic acid, and the cyclooxygenases-1 and -2 (COX-1 and COX-2).

Lithium diet fed rats showed statistically significant lesser increase in body weight as compared to the rats fed control diet as determined at day 14 and 21; lithium feeding resulted in approximately two fold increase in water intake; lithium feeding caused 2 to 3-fold increase in urine output associated with a comparable 3-fold decrease in urine osmolality at day 14 and 21; lithium feeding resulted in marked reduction in protein abundance of AQP2 water channel in inner medulla, whose values were 15-20% of the mean values seen in rats fed control diet. The urine parameters and AQP2 protein abundance in lithium diet fed rats presented here are quite comparable to those obtained by the groups of Søren Nielsen and Mark Knepper on lithium model (Marples et al, 1995; Kwon et al. 2000). Furthermore, it was observed that the rats tolerated lithium in the diet well without any signs of gastrointestinal disturbances or morbid condition.

TABLE 6

Primers for real-time RT-PCR

| Gene | Primer Pairs | Amplicon Size, bp | Annealing Temp. ° C. |
|---|---|---|---|
| AQP2 | F: 5'-GGGTTGCCATGTCTCCTTTCCTTCG<br>R: 5'-CCAGGTCCCCACGGATTTCT | 118 | 60 |
| P2Y2-R | F: 5'-ACCCGCACCCTCTATTACTCCTTC<br>R: 5'-AGTAGAGCACAGGGTCAAGGCAAC | 129 | 60 |
| V2-R | F: 5'-TTGCCTTGATGGTGTTTGTG<br>R: 5'-CACCAGACTGGCGCGTGTATCT | 85 | 58 |
| cPLA2 | F: 5'-GCACATAATAGTGGAACACC<br>R: 5'-ACACAGTGCCATGCTGAACC | 410 | 58 |
| COX-1 | F: 5'-TAAGTACCAGGTGCTGGATGG<br>R: 5'-GGTTTCCCCTATAAGGATGAG | 244 | 58 |
| COX-2 | F: 5'-TACAAGCAGTGGCAAAGGCC<br>R: 5'-CAGTATTGAGGAGAACAGATGGG | 283 | 62 |
| EP3-R | F: 5'-ACGTCCGTCTGCTGGTC<br>R: 5'-CCTTCTCCTTTCCCATCTG | 100 | 60 |
| GAPDH | F: 5'-CTACATGTTCCAGTATGACTCTA<br>R: 5'-GAGTGGCAGTGATGGCATGGACT | 421 | 57 |
| β-Actin | F: 5'-CACTGTGTTGGCATAGAGGTC<br>R: 5'-AGAGGGAAATCGTTGCGTGACA | 275 | 66 |

3. Example 3: Observation on the Purinergic and Prostanoid Interactions in Bilateral Ureteral Obstruction (BUO)-Induced Nephrogenic Diabetes Insipidus In addition to the lithium-induced NDI model, the NDI model induced by bilateral ureteral obstruction (BUO) and release has been established. FIG. 8 depicts the characterization of the BUO model. Male Sprague-Dawley rats were subjected to either BUO for 24 hours and release (N=8) or sham operation (N=7) following the protocol published by the groups of Søren Nielsen and Mark Knepper (Sonnenberg and Wilson, 1976; Frøkiær et al, 1996). Rats were anesthetized with 3-5% Isofluorane using rodent anesthesia machine, and placed on a heated pad to maintain body temperature close to 37° C., as monitored by an electronic rectal probe. Hair on the abdomen was clipped and the skin was cleaned using a preventive antiseptic. The following procedures were conducted under aseptic conditions. A midline abdominal incision was made and both ureters were exposed one after another. A 5 mm-long piece of bisected polyethylene tubing (PE-50; Clay Adams) was placed around the mid portion of each ureter. The ureter was then occluded by gently tightening the tubing with 5-0 silk ligature. The abdominal wall was closed in layers. The entire surgical procedure—skin to skin—took about 20 to 40 min in our hands. Animals recovered within 5 min of shutting off Isolfuorane flow. Sham operated rats underwent similar procedure (laparotomy and handling of ureters), but their ureters were not occluded with PE tubing and silk. Twenty-four hours later, the abdomen was opened again under Isofluorane anesthesia, and the obstructed ureters, which were clearly enlarged proximal to the PE tubing ligature, were decompressed by gently removing the silk ligature and PE tubing. With this technique, the ureters were completely occluded for 24 hours and released, without any evidence of subsequent functional impairment of ureters. Within a few minutes after recovery from anesthesia, the BUO rats passed urine.

The sham operated rats also underwent a second laparotomy 24 hours later. During both surgical procedures, about 5 ml of warm sterile normal saline (USP grade) was instilled into the abdominal cavity before closure to compensate for loss of fluids due to surgical procedure. On both occasions, morphine-derived pain reliever (Buprenorphin 0.05 mg/kg subcutaneously) was administered before the animals recovered from the anesthesia. Buprenorphine dose was repeated at 12-hour intervals during the first two post-operative days. Animals were monitored at frequent intervals for signs of pain, distress and significant degree of weight loss or gain. With this procedure, all animals completely recovered from the post-surgical stress within a couple of days and remained active and alive until euthanized. No significant differences in the body weights of the BUO rats as compared to their age/batch matched sham operated rats were noted. However, the kidneys of BUO rats were enlarged and were approx. 1.5- to 2-fold larger than the kidneys of age/batch matched sham operated rats, with cortex and outer medulla accounting for most of the enlargement. Animals were euthanized either on day 7 (for functional studies) or day 12 (for molecular studies), counting from the day of second surgical procedure when the ureteral obstruction was released.

4. Example 4: The Temporal Sequence and Nature of Molecular and Functional Events that Reflect the Accentuated Interaction Between Purinergic and Prostanoid Systems, and their Relation to the Vasopressin System in the Development of Acquired NDI Previous studies demonstrated increased production of renal PGE2 in acquired NDI, which may play a critical role in the genesis and maintenance of polyuria. Independent of these potent and accentuated interactions, both PGE2 and extracellular nucleotides (purinergic agonists) have been shown to antagonize AVP action on the IMCD. In acquired NDI the circulating levels of AVP are either normal or elevated, but the collecting duct does not respond to AVP. A temporal sequence of molecular and functional events of purinergic and prostanoid interactions can be constructed, and examined to detect how these interactions oppose or neutralize the vasopressin action on IMCD resulting in acquired NDI.

A comprehensive analysis of the status of purinergic, prostanoid and vasopressin systems in acquired NDI models as a function of time is shown, and thus construct a molecular and functional correlation of interactions among these systems. The relationship between purinergic and prostanoid interactions and their relation to vasopressin system in acquired NDI can be studied by measuring how they are affected or disrupted by the administration of indomethacin, which is known to ameliorate polyuria of NDI by inhibiting the synthesis of PGE2. Since indomethacin has been shown to reverse the polyuria of acquired NDI both in humans and in experimental animals, by performing these reversal studies one can determine whether accentuated purinergic and prostanoid interactions are responsible for the vasopressin-resistant polyuria in acquired NDI. The reversal of polyuria by indomethacin can be accompanied by reversal of accentuated interactions between the purinergic and prostanoid systems.

A determination of the expression of mRNA and/or protein of P2Y2, V2 and EP3 receptors by real-time RT-PCR, in situ hybridization, Western blotting and immunohistochemistry is made. Determination of cellular cAMP and protein kinase A activity by commercial assay kits is also made. Determination of in vitro ATP release from microdissected IMCD as described earlier (Schwiebert and Kishore, 2001) is also carried out. NDI rats of lithium and BUO model at all time points stated above are used.

Determination of the protein abundance and apical membrane targeting of AQP2 water channel using semi-quantitative immunoblotting and immunohistochemistry, respectively, is carried out. Determination of cellular and subcellular distributed of P2Y2 receptor protein by immunohistochemistry and confocal microscopy is done. For these studies, NDI rats of lithium and BUO models at all time points are used.

Examination of expression, DNA binding activity and phosphorylation of CREB (cAMP responsive element binding protein), known to be involved in the transcriptional regulation of AQP2 gene, is carried out. The expression of CREB mRNA and protein is determined by real-time RT-PCR and Western blotting, respectively. The DNA binding activity of CREB to the Cre (cAMP responsive element) site in the AQP2 promoter is determined by EMSA (electromobility shift assay). The extent of CREB phosphorylation at $Ser^{133}$ can be determined by immunoblotting.

The effect of administration of indomethacin, a non-specific inhibitor of cyclooxygenases, is examined for its role in the purinergic and prostanoid interactions, and their relation to vasopressin system in lithium and BUO models at defined time points. Groups of control or sham operated rats are also be administered with indomethacin for comparative purpose. Indomethacin is administered at a dose of 2 mg/kg/day by gavage in two divided doses or in gel. Urine output and osmolality is monitored daily, and the rats are euthanized when these parameters in NCI rats are returned to their corresponding untreated control or sham operated levels. Samples of kidney tissue and urine are collected and processed as described above. In vitro microperfusion of IMCD is performed to assess the basal and AVP-stimulated response following indomethacin treatment. The data obtained from the indomethacin-treated NDI rats is compared to the corresponding data obtained from the untreated NDI rats and control or sham operated rats with or without indomethacin treatment.

The NDI rats not subjected to indomethacin treatment, can display accentuated interactions between purinergic and prostanoid systems. A gradual decrease in cellular cAMP levels, associated with increasing response of IMCD to purinergic-mediated in vitro PGE2 release, can be seen. The declining cellular cAMP levels and accentuating purinergic and prostanoid interactions can be accompanied by decreased transcriptional activation of AQP2 gene, decreased abundance and apical membrane targeting of AQP2 protein, which directly correlates with decreased basal and AVP-stimulated water transport in isolated microperfused IMCD. Changes in the protein abundance and cellular/subcellular distribution of P2Y2 receptor protein during the development of NDI can also be observed. As the NDI progresses, metabolic and structural alterations can occur, accompanied by involvement of cytokines and other mediators.

5. Example 5: Purinergic and Prostanoid Interaction with the Vasopressin System The expression, phosphorylation, apical membrane targeting and retrieval of AVP-regulated AQP2 water channel in the collecting duct principal cell are dependent on the cellular cAMP levels and the activity of protein kinase A. In order to understand how the accentuated interactions between purinergic and prostanoid systems in acquired NDI translates into disruption of the AVP-mediated functional effects, the intracellular signaling mechanisms whereby these two systems interact with each other, and with the vasopressin system in IMCD in reducing the cAMP levels to a critical level so as to cause a marked decrease in the expression of AQP2 protein and reduction in the water transport capability of IMCD can be elucidated. Thus, the molecules play key roles either directly or indirectly in the regulation of cellular cAMP levels, which is a critical factor for the transcriptional regulation and membrane targeting of vasopressin-regulated AQP2 water channel in collecting duct principal cell, as schematically illustrated in FIG. 10 and FIG. 2. As illustrated in FIG. 10, the two key sites that can result in decreased cellular cAMP levels are: (i) decreased production of cAMP by enhancement of the activity of Gi (via an action of PKC), and/or inhibition of the activity or decreased expression of a key form of adenylyl cyclase (AC), or (ii) rapid hydrolysis of cAMP by the increased activity of phosphodiesterases (PDEs).

Furthermore, inbred mice (Di +/+) with constitutively active cAMP-PDE (type IV) are polyuric with low cellular cAMP levels and AQP2 in inner medulla (Homma et al, 1991; Frøkiær et ak, 1999). While the Di +/+ mice can represent an inherited abnormality, rats made polyuric due to hypercalcemia induced by vitamin D can have this condition prevented by the administration of specific inhibitors of PDE isoforms type III and IV, indicating that increased activity of PDEs may also be involved in certain forms of acquired NDI (Wang et al, 2002). Another potential pathway for antagonizing the AVP action on medullary collecting duct is enhanced release of arachidonic acid due to the stimulation of phosphoinositide signaling pathway. As discussed above, the availability of arachidonic acid is the rate-limiting step in the synthesis of prostaglandins by cyclooxygenases (COX). It has been shown that there are large and significant increases in the mRNA expression of cPLA2 and/or COX-1 and COX-2 in NDI models.

The expression and/or activities of key molecules that cause a decrease in cellular cAMP levels in the kidneys of NDI rats of lithium and BUO models is assessed. NDI and control or sham operated rats are then chronically infused with two different doses of dDAVP, a V2 receptor-specific analogue of vasopressin, at 5 or 20 ng/h for 5 days via Alzet mini-osmotic pumps (Kishore et al, 1996, 2004), and then examined for how the expression and/or activities of these molecules are modulated by increasing doses of dDAVP in the face of accentuated interaction of purinergic and prostanoid systems. This situation mimics several clinically relevant acquired NDI conditions, where the circulating vasopressin concentrations are either normal or high, and yet there is lack of response of kidney to it.

mRNA expression and protein abundance of AC5 and AC6 are assessed using real-time. RT-PCR and Western blotting, respectively. The total activity of AC and she activities of type III and IV PDEs can be measured in renal medulla according to the methods described by Murthy et al (2002) and Takeda et al (1991), respectively.

Figure 12:
FIG. 12 shows the determination of the degree of phosphorylation of cPLA2. It is achieved by prolonged low voltage PAGE electrophoresis of solubilized tissue homogenates, so that the native and phosphorylated species clearly separate, and then transferring the separated proteins to a nitrocellulose membrane and immunoblotting with a specific antibody to cPLA2. Figure shows native (red arrow) and phoshorylated cPLA2 (blue arrow) in inner medullary homogenates of 5 normal rats separated in our laboratory using PAGE and immunoblotting.

The mRNA and protein expression of cPLA2, iPLA2, COX-1 and COX-2 by real-time RT-PCR and Western blotting, respectively, and assay the activities of cPLA2 and iPLA2 in inner medulla by commercial kits are carried out. The degree of phosphorylation of cPLA2 is determined by Western analysts as shown in FIG. 12. In vitro studies are also carried out on IMCD preparations to identify which phospholipases are involved in the purinergic-mediated PGE2 release. For the generalized inhibition of phospholipases, Aristolochic acid (100 and 200 µM) and Quinacrine (10 or 30 µM) are used, cPLA2 is inhibited by AACOCF3 (30 or 60 µM) or Pyrrophenone (10, 20 or 50 nM). iPLA2 is inhibited by Bromoenol lactone (BEL; 0.5 or 3 µM) and PACOCF3 (10, 20 or 100 µM). For the inhibition of cyclooxygenases in IMCD preparations. Flurbiprofen (30 and 300 µM) and APHS (10 said 20 µM) are used, both non-specific COX inhibitors. COX-1 activity is inhibited by Valeroyl salicylate (30 and 300 µM). COX-2 activity is inhibited by NS-398 (10 and 30 µM).

PKC is a family of isoforms—the classic, the novel, and the atypical—depending on their sensitivity to $Ca^{2+}$, phospholipids and diacylglycerol (Nishzukha, 1992). Rat IMCD expresses one classic isoform ($\alpha$), three novel isoforms ($\delta$, $\epsilon$, $\eta$), and one atypical isoform ($\zeta$) (Chou et al, 1998). However, following the activation of PI signaling pathway by the muscarinic cholinergic agent, carbachol, only PKC isoform $\eta$ translocates to the membrane from cytosol, indicating its specific activation (Chon et al, 1998). The specific PKC isoform(s) is (are) activated in the inner medulla in NDI and the effect of dDAVP infusion on it are identified. In vitro studies on IMCD of NDI rats are also conducted with or without dDAVP treatment to assess the effect of purinergic stimulation on the expression and activity of PKC isoforms. These studies are achieved by isolating membrane and soluble fractions by centrifugation, and then immunoblotting them using commercially available specific antibodies to PKC isoforms to determine their translocation from cytosol to membrane, as described by Chou et al (1998). The activities of JNK1, ERK and p38 MAP kinases are determined as described (Sheikh-Hamad et al, 2004). The activities of MAP kinases in vitro in IMCD suspensions are inhibited by PD98059 (10 µM; for MEK), SP600125 (10 µM; for JNK1), U-0126 (10 µM); for ERK), and SB202190 (10 µM; for p38).

A significant decrease in the cellular c-AMP levels in NDI rats can be seen. This is similar to what is seen in NDI patients in the clinic. The decreased cellular cAMP levels can be due to either decreased formation or increased breakdown of cAMP of both. These changes can be in turn due to the increased expression and activity of molecules that oppose the action of vasopressin on collecting duct either directly or indirectly. In a rat model of chronic dDAVP infusion it was observed that the mRNA expression and protein abundance of P2Y2 receptor are significantly down-regulated to 54% and 49%, respectively. On the other hand, the expression of V2 receptor mRNA did not change significantly (Kishore et al, 2004). It appears that under normal conditions the AVP system can override the purinergic system and decrease the P2Y2 receptor mRNA and protein expression.

6. Example 6: Treating Acquired NDI by Blocking the Accentuated Interactions Between the Purinergic and Prostanoid Systems in the IMCD Prostaglandins appear to play a critical role in the genesis of polyuria in acquired NDI. The targets for blocking the accentuated interactions between purinergic and prostanoid systems and the effects of these interactions are P2Y2 purinergic and/or EP3 prostanoid receptors, both expressed in IMCD. Antagonists such as suramin, reactive blue 2, and PPADS (pyrodoxal phosphate-6-azophenyl 2',4'-disulfonic acid) can antagonize several subtypes of P2Y receptor family (Schwiebert and Kishore, 2001). Other P2Y2 antagonists can be identified by (i) testing their in vitro efficacy in blocking the purinergic-mediated PGE2 release from the IMCD of normal and hydrated rats; (ii) testing their in vivo safety and toxicity; (ii) studying pharmacokinetics and optimal dose response, regimen and route of administration, and (iii) testing in vivo efficacy in blocking the purinergic and prostanoid interactions as assessed ex-vivo, using IMCD preparations freshly obtained from normal and hydrated rats that had been previously treated with these agents. Selected agents are then administered to NDI rats of lithium and BUO models to block the accentuated interactions of purinergic and prostanoid systems. Additional groups of control and sham operated rats also receive these agents for comparative purpose. Following the administration of P2Y2 receptor antagonists to NDI rats changes in urinary parameters are monitored and the rats are euthanized when their urine parameters are comparable to the untreated control or sham operated rats, just as with indomethacin treatment. In addition to determining the expression and activity of molecules in the kidney, in vitro microperfusion of IMCD is performed to directly assess the functional status and response to AVP in NDI rats following the treatment with P2Y2 receptor antagonists. The effect of administration of P2Y2 receptor "agonists" on the course of NDI in rats using the same urine and kidney parameters as proposed for the P2Y2 receptor antagonists is also established. These P2Y2 receptor agonists can worsen the polyuric condition in NDI models. Indomethacin can then be administered to these NDI rats with worsened polyuric condition due to the administration of P2Y2 receptor agonists, and examined for whether indomethacin can ameliorate the worsened polyuric condition.

The effect of blockade of EP3 prostanoid receptor in the NDI rats as EP3 receptor is another target for the blockade of purinergic and prostanoid interactions. ONO-8711, a combined EP3 and EP1 receptor antagonist, can be used in NDI rats to compare the effects obtained with it to the effects seen in the NDI rats that receive ONO-8712, a selective EP1 receptor antagonist. Thus, the effects of selective blockade of EP1 in NDI rats from effects of the combined blockade of EP1 and EP3 receptors can be seen.

Apart from the above, protocols, combinations of P2Y2 receptor antagonist(s) with either EP1 and EP3 receptor blockers or low doses of COX-2 specific inhibitors (rofecoxib or celecoxib) or phosphodiesterease inhibitors (rolipram and milrinone) or thiazide and amiloride can be administered in combination therapy with P2Y2 receptor antagonists.

7. Example 7: Apyrase Prevents Increase in Urine how Induced by Lithium

Potato apyrase (EC 3.6.1.5) is a soluble NTPDase, exhibiting both ATPase and ADPase activities. It is non-toxic and safe to administer either intravenously or intraperitoneally. Two experiments were conducted. In one experiment Sprague-Dawley rats were divided into two groups (N=4 per group). One group was fed with regular rat chow, while the other was fed regular rat chow to which Lithium Chloride was added to a concentration of 40 mmol/kg wt of the food. Both groups were fed for 14 days without any other treatment. The second experiment was similar to the first one, except that potato apyrase (Sigma Chemical Co) was administered to both regular and lithium-added diet fed rats front day 7 to day 14 at a dose of 100 units/kg body wt. intraperitoneally, three times a day (~8 hourly intervals). All rats had free access to drinking water. Twenty-four hour urine samples were collected from all rats on day 7 and 14 prior to euthanasia, and analyzed. All rats were euthanized on day 14, and IMCD suspensions were prepared. Basal and ATPγS-stimulated ex vivo PGE2 release by IMCD was determined as per the methods previously established. The results are shown in FIG. 13.

Figure 13:
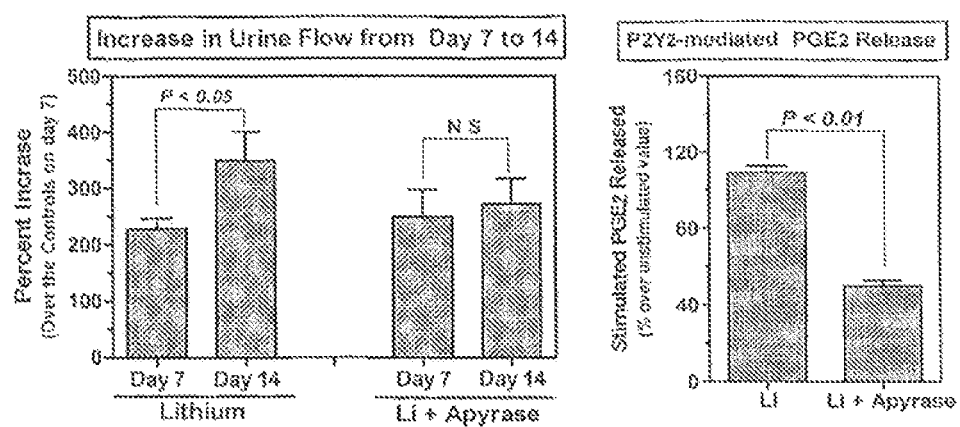
FIG. 13 shows the effect of depletion of extracellular ATP by apyrase treatment on the urine flow (left panel) and on and P2Y2 receptor-stimulated ex vivo PGE2 release by IMCD (right panel).
Figure 14:
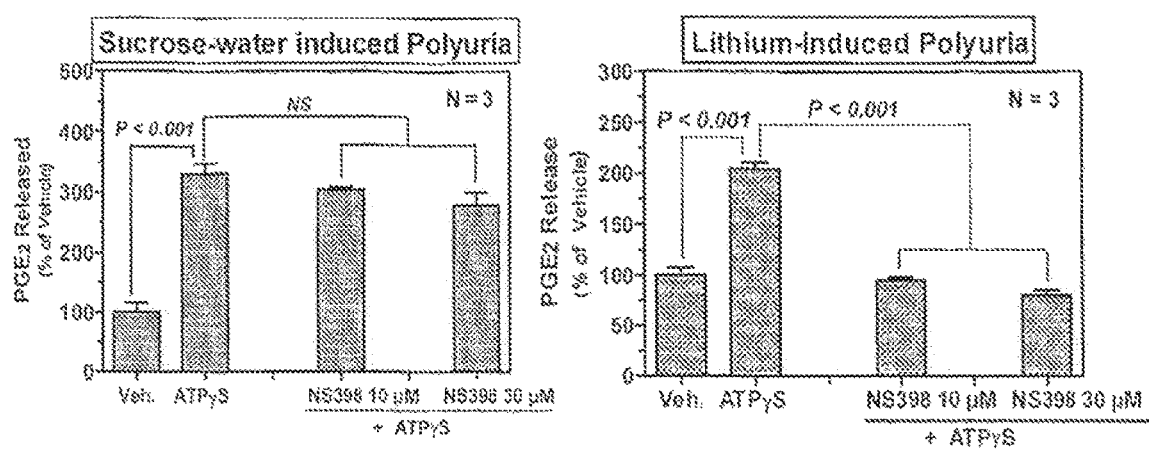
FIG. 14 shows dependency on the COX-2 activity of P2Y2 receptor-mediated PGE2 release by IMCD in lithium-induced NDI (right panel) and the lack of such dependency on the activity of COX-2 in sucrose-water induced polyuria (left panel).

As documented in FIG. 13, apyrase treatment from day 7 to 14 in lithium-fed rats (i) prevented further increase in the urine flow induced by lithium, and (ii) significantly decreased the P2Y2 receptor-stimulated PGE2 release by IMCD as compared to the apyrase-untreated and lithium-fed rats. Apyrase treatment did not change the urine output or P2Y2-mediated PGE2 release by IMCD in control rats fed with regular diet. These observations opened the possibility to decrease the PGE2 formation in acquired NDI by novel means other than the direct inhibition of the activities of cyclooxygenases.

Apyrase has been successfully used for blocking the purinergic signaling, especially following xenograft (Koyamada et al, 1996). Apyrase can be optimized for administration alone or in combination with specific P2Y2 receptor antagonists to achieve the best possible effect in controlling polyuria and hypernatremia.

8. Example 8: Dependency on the COX-2 Activity of P2Y2 Receptor-Mediated PGE2 Release by IMCD Freshly isolated IMCD preparations were stimulated with 50 μM ATPγS alone or in the presence of a COX-2-specific inhibitor, NS398 (10 or 30 μM). PGE2 released into the medium was assayed and normalized to the protein content. Results (mean±SE) of triplicate incubations were presented as percent of values in vehicle control (no added agents). In both series of experiments, PGE2 release from IMCD in incubations with only NS398 (10 or 30 μM) was similar to the corresponding vehicle controls. Data for sucrose-water induced polyuria in rats shown are adapted from Sun et al, (2005). Data for lithium-induced polyuria were generated by feeding rats with either regular diet or lithium-added diet for 14 days. Lithium-fed rats developed polyuria associated with marked decrease in AQP2 protein abundance in inner medulla. These observations indicate that signaling through P2Y2 receptor is dynamic, and depends on the underlying condition or pathophysiology.

Figure 15:
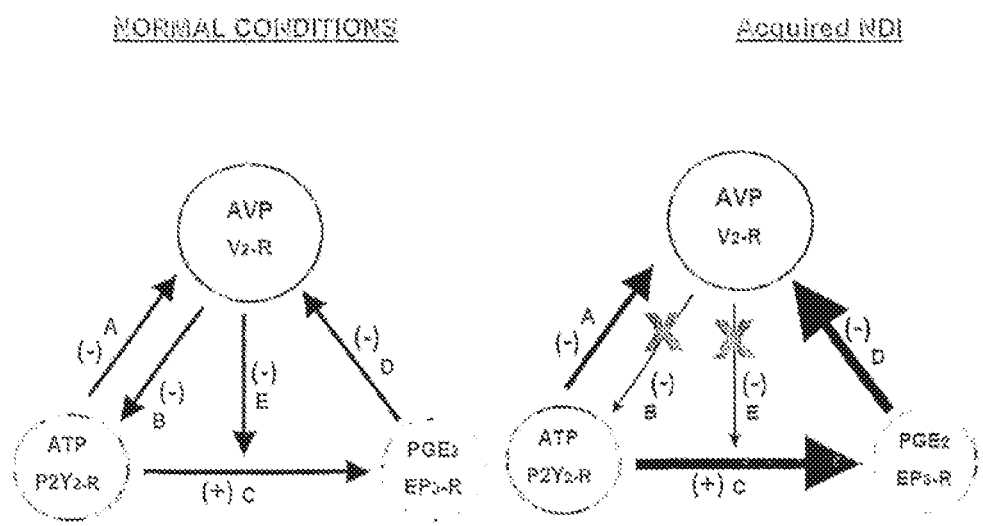
FIG. 15 shows the proposed models for the interaction among vasopressin (AVP), purinergic (ATP), and prostanoid (PGE2) systems in medullary collecting duct principal cell under normal conditions (left) and how they are deranged in acquired NDI (right). (−) and (+) signs denote inhibition and stimulation respectively. X marks indicate blocked pathways. Larger size of the arrows indicates accentuation of pathways. The letters A, B, C, D and E are keyed to the explanation in Example 9.

Example 9: the Interaction Among Vasopressin (AVP), Purinergic (ATP), and Prostanoid (PGE2) Systems in Medullary Collecting Duct Principal Cell Under Normal and NDI Conditions The following explanations correspond with FIG. 15.

A. Acute Interaction of Purinergic System with AVP: In an acute model of in vitro microperfused medullary collecting ducts from normal animals, it was demonstrated that activation of P2Y2 receptor down regulates the AVP-stimulated water flow (Kishore et al, 1995; Rouse et al, 1994). This interaction can remain intact or accentuated in the acquired NDI.

B. Chronic Interaction of AVP with Purinergic System: It was observed that chronically elevated circulating AVP levels arising from subjecting normal rats to dehydration or dDAVP infusion, down regulates the expression P2Y2 receptor (Kishore et al, 2005; Sun et al, 2005b). This chronic effect of AVP is obviously blunted in acquired NDI where collecting duct is resistant to vasopressin. This is supported by data, where it was observed that the expression of P2Y2 receptor did not change significantly in acquired NDI models.

C. Purinergic-mediated Prostanoid Production: It was observed that activation of P2Y2 receptor in ex vivo preparations of medullary collecting ducts from normal rats results in production and release of PGE2 (Welch et al, 2003). This response is markedly accentuated in rats with physiological polyuria induced by sucrose-water drinking (Sun et al, 2005a). This interaction is also accentuated in acquired NDI, resulting in increased purinergic-mediated PGE2 production by IMCD.

D. Interaction between PGE2 with AVP System: There exists an inhibitory effect of PGE2 on AVP-induced water flow in the collecting duct, and the AVP-induced trafficking of AQP2 water channel to apical plasma membrane (Nadler et al, 1992; Han et al, 1994; Roman and Lechene, 1981; Rouch and Kudo, 2000; Zelenina et al, 2000). Increased production of PGE2 in acquired NDI obviously results in potent inhibition of AVP action leading to vasopressin resistant state. This is further supported by the fact that blocking the synthesis of PGE2 by indomethacin prevented the polyuria of acquired NDI (Okshe and Rosenthal, 1998).

E. Chronic Effect of Elevated Circulating AVP Levels on Purinergic-driven PGE2 Production: In normal rats chronically infused with higher doses of dDAVP (20 ng/h) or in dehydrated rats it was observed that the purinergic-driven PGE2 production by IMCD is significantly decreased (Sun et al, 2005b). This effect is obviously blunted in acquired NDI, as we documented that purinergic-mediated prostanoid production is actually increased in acquired NDI models, similar to the human patients. The circulating AVP levels in acquired NDI are either normal or elevated.

F. Sequences

```
AQP2
                                      SEQ ID NO: 1
F: 5'-GGGTTGCCATGTCTCCTTTCCTTCG

AQP2
                                      SEQ ID NO: 2
R: 5'-CCAGGTCCCCACGGATTTCT

P2Y2-R
                                      SEQ ID NO: 3
F: 5'-ACCCGCACCCTCTATTACTCCTTC

P2Y2-R
                                      SEQ ID NO: 4
R: 5'-AGTAGAGCACAGGGTCAAGGCAAC

V2-R
                                      SEQ ID NO: 5
F: 5'-TTGCCTTGATGGTGTTTGTG

V2-R
                                      SEQ ID NO: 6
R: 5'-CACCAGACTGGCGCGTGTATCT cPLA2
                                      SEQ ID NO: 7
F: 5'-GCACATAATAGTGGAACACC cPLA2
                                      SEQ ID NO: 8
R: 5'-ACACAGTGCCATGCTGAACC

COX-1
                                      SEQ ID NO: 9
F: 5'-TAAGTACCAGGTGCTGGATGG

COX-1
                                      SEQ ID NO: 10
R: 5'-GGTTTCCCCTATAAGGATGAG

COX-2
                                      SEQ ID NO: 11
F: 5'-TACAAGCAGTGGCAAAGGCC

COX-2
                                      SEQ ID NO: 12
R: 5'-CAGTATTGAGGAGAACAGATGGG

EP3-R
                                      SEQ ID NO: 13
F: 5'-ACGTCCGTCTGCTGGTC

EP3-R
                                      SEQ ID NO: 14
R: 5'-CCTTCTCCTTTCCCATCTG

GAPDH
                                      SEQ ID NO: 15
F: 5'-CTACATGTTCCAGTATGACTCTA

GAPDH
                                      SEQ ID NO: 16
R: 5'-GAGTGGCAGTGATGGCATGGACT

β-Actin
                                      SEQ ID NO: 17
F: 5'-CACTGTGTTGGCATAGAGGTC β-Actin
                                      SEQ ID NO: 17
R: 5'-AGAGGGAAATCGTTGCGTGACA
```

G. Literature Cited

Agre P. Aquaporin water channels in kidney, J Am Soc Nephrol 11:764-777, 2000

Bao Y, Pucci M L, Chan B S, Lu R, Ito S and Schuster V L. Prostaglandin transporter PGT is expressed in cell types that synthesize and release prostanoids. Am J Physiol. Renal Physiol 282:F1103-F1110, 2002

Bell T N. Diabetes insipidus. Crit Care Nurs Clin North Am 6:675-685, 1994

Bonventre J V. Phospholipase A2 and signal transduction. J Am Soc Nephrol 3:128-150, 1992

Bonventre J V, and Nemenoff R. Renal tubular arachidonic acid metabolism. Kidney Int 39; 438-449, 1991

Breyer D B, and Breyer R M. Prostaglandin E receptors and the kidney. Am J Physiol. Renal Physiol 279:F12-F23, 2000

Chou C-L, Rapko S I, and Knepper M A. Phosphoinositide signaling in rat inner medullary collecting duct. Am J Physiol: Renal Physiol 274:f564-F572, 1998

Communi D, Janssens R, Suarez-Huerta N, Robaye B, and Boeynaems J M. Advances in signaling by extracellular nucleotides, the role and transduction mechanisms of P2Y receptors. Cell Signal 12:351-360, 2000

DiGiovanni S R, Nielsen S, Christensen E I, and Knepper M A. Regulation of collecting duct water channel expression by vasopressin in Brattleboro rat. Proc Natl Acad Sci. USA 91:8984-8988, 1994

Di Renzo G C, Johnston J M, Okazaki T, Okita J R, MacDonald P C and Bleasdale J E. Phosphatidylinositol-specific phospholipase C in fetal membranes and uterine deciduas. J Clin Invest 67:847-856, 1981

Ecelbarger C A, Maeda Y, Gibson C C and Knepper M A. Extracellular ATP increases intracellular calcium in rat terminal collecting duct via a nucleotide receptor. Am J Physiol (Renal) 267: F998-F1006, 1994

Ecelbarger C A, Yu S, Lee A J, Weinsten L S and Knepper M A. Decreased renal Na—K-2Cl cotransporter abundance in mice with heterozygous disruption of the Gsα gene. Am J Physiol. Renal Physiol 277:F235-F244, 1999

Ecelbarger C A, Sands J M, Doran J J, Cacini W, and Kishore B K. Expression of salt and urea transporters in rat kidney during cisplatin-induced polyuria. Kidney Int 60:2274-2282, 2001

Endo S, Nomura T, Chan B S, Lu R, Pucci M L, Bao Y and Schuster V L. Expression of PGT in MDCK cell monolayers: Polarized apical localization and induction of active PG transport. Am J Physiol. Renal Physiol 282: F618F622, 2002

Enjyoji K, Sévígny J, Lin Y, Frenette P S, Christie P D, A M Esch II J S, Imai M, Edelberg J M, Rayburn H, Lech M, Beeler D, Csizmadia E, Wagner D D, Robson S C, and Rosenberg R D. Targeted disruption of cd39/ATP diphosphohydrolase results in disordered hemostasis and thromboregulation. Nature Med 5:1010-1017, 1999

Fradet Y, Simard J, Grose J H, and Lebel M. Enhanced urinary prostaglandin E2 in postobstructive diuresis in humans. Prostaglan Med 5:20-30, 1980

Fradet Y, Lebel M, Grose J H, Talbot J, and Charrois R, Renal prostaglandins in postobstructive diuresis. Comparative study of unilateral and bilateral obstruction in conscious dogs. Prosta Leukot Essen Fatty Acids 31:123-129, 1988

Frøkiær J, Marples D, Knepper M A, and Nielsen S. Bilateral ureteral obstruction downregulates expression of vasopression sensitive AQP-2 water channel in rat kidney. Am J Physiol. Renal Physiol 270:F657-F668, 1996

Frøkiær J, Marples D, Knepper M A, and Nielsen S. Pathophysiology of aquaporin-2 in water balance disorder. Am J Med Sci 316:291-299, 1998

Frøkiær J, Marples D, Valtin H, Morris J F, Knepper M A, and Nielsen S. Low aquaporin-2 levels in DI +/+ sever mice with constitutively high cAMP-phosphodiesteras activity. Am J Physiol; Renal Physio 276: F179-F190, 1999

García-Villalba P, Denkers N D, Wittwer C T, Hoff C, Nelson R D, and Mauch T J. Real-time PCR quantification of AT1 and AT2 angiotensin receptor mRNA expression in the developing rat kidney. Nephron Exp Nephrol 94:154-159, 2003

Gitlin M. Lithium and the kidney: and updated review. Drug Saf 20:231-243, 1999

Han J S, Maeda Y, Ecelbarger C, and Knepper M A. Vasopressin-independent regulation of collecting duct water permeability. Am J Physiol. Renal Physiol 266: F139-F146, 1994

Homma S, Gapstur S M, Coffey A, Valtin H and Dousa T P. Role of cAMP-phosphosdiesterase isoenzymes in pathogenesis of murine nephrogenic diabetes insipidus. Am J Physiol: Renal Physiol 261:F345-F353, 1991

Hozawa S, Holtzman E J and Ausiello D. cAMP motifs regulating transcription in aquaporin-2. Am J Physiol. Cell Physiol 270:C1695-C1702, 1996

Inscho E W. Renal microvascular effects of P2 receptor stimulation. Clin Exp Pharmacol Physiol 28:332-339, 2001

Ivanov A I, Pero R S, Scheck A C and Romanovsky A A. Prostaglandin E2-synthesizing enzymes in fever: differential transcriptional regulation. Am J Physiol (Regal Integr Comp Physiol) 283:R1104-R1117, 2002

Kishore B K, Chou C-L, and Knepper M A. Extracellular nucleotide receptor inhibits AVP-stimulated water permeability in inner medullary collecting duct. Am J Physiol. Renal Physiol 269:F863-F869, 1995

Kishore B K, Ginns S M, Krane C M, Nielsen S, and Knepper M A. Cellular localization of P2Y2 purinoceptor in rat renal inner medulla and lung. Am J Physiol. Renal Physiol. 278:F43-F51, 2000a Kishore B K, Krane C M, Diluilo D, Menon, A G, and Cacini W. Expression of renal aquaporins 1, 2 and 3 in a rat model of cisplatin-induced polyuria. Kidney Int 58:701-711, 2000b Kishore, B K, Miller R L, Shi H, Zhang P and Nelson R D. Chronic dDAVP infusion in rats causes decreased expression of P2Y2 receptor mRNA and protein in inner medulla. (Abstract) Annual Meeting of the American Society of Nephrology, St. Louis, Mo., October-November 2004

Kishore B K, Krane C M, Miller R L, Shi H, Zhang P, Hemmert A, Sun R, and Nelson R D. P2Y2 receptor mRNA and protein expression is altered in inner medullae of hydrated and dehydrated rats: Relevance to AVP-independent regulation of IMCD function. Am J Physiol Renal Physiol 288:F1164-F1172, 2005

Kishore B K, Terris J M, and Knepper M A. Quantitation of aquaporin-2 abundance in microdissected collecting ducts: Axial distribution and control by AVP. Am J Physiol: Renal Physiol 269:F62-F70, 1996

Kishore B K, Chou C-L, and Knepper M A. Extracellular nucleotide receptor inhibits AVP-stimulated water permeability in inner medullary collecting duct. Am J Physiol: Renal Physiol 269:F863-F869, 1995

Kohan D E, and Hughe K. Autocrine role of endothelin in rat IMCD: Inhibition of AVP-induced cAMP accumulation. Am J Physiol. Renal Physiol 265:F126-F129, 1993

Koyamada N. Miyatake T, Candinas D, Hechenleitner P, Siegel J, Hancock W W, Bach F H, and Robson S C. Apyrase administration prolongs discordant xenograft survival. Transplantation 62:1739-1743, 1996

Krane C M, and Kishore B K, Aquaporins; the membrane water channels of the biological world. Biologist 50:81-86, 2003

Kwon T-H, Laursen U H, Marples D, Maunsbach A B, Knepper M A, Frøkiær J, and Nielsen S. Altered expression of renal AQPs and $Na^+$ transporters in rats with lithium-induced NDI. Am J Physiol. Renal Physiol 279: F552-F564, 2000

Laszlo K, Juskzko J, and Balint P. Prostaglandin-dependent changes in renal haemodynamics and excretory patterns before and after release of 24 hours bilateral ureteral ligation. Acta Physiol Acad Sci Hung 56:309-323, 1980

Laycock J F and Hanoune J. From vasopressin receptor to water channel: intracellular traffic, constraints and by-pass. J Endocrinol 159:361-372, 1998

Lenox R H, McNamara R K, Papke R L, and Manji H K. Neurobiology of lithium. J Clin Psychiatry 58:37-47, 1998

Li C, Wang W, Kwon T-H, Knepper M A, Nielsen S, and Frøkiær J. Altered expression of major renal Na transporters in rats with bilateral ureteral obstruction and release of obstruction. Am J Physiol. Renal Physiol. 285:F889-F901, 2003

Li C, Klein J D, Wang W, Knepper M A, Nielsen S, Sands J M, and Frokiær J. Altered expression of urea transporters in response to ureteral obstruction. Am J Physiol. Renal Physiol. Feb. 24, 2004 [Epub ahead of print]

Lin L-L, Wartmenn M, Lin A Y, Knopf J L, Seth A, and Davis R J. cPLA2 is phosphorylated and activated by MAP kinase. Cell 72:269-278, 1993

Marples D, Christensen S, Christensen E I, Ottosen P D, and Nielsen S. Lithium-induced downregulation of aquaporin-2 water channel expression in rat kidney medulla. J Clin. Invest 95:1838-1845, 1995

Matsumura Y, Uchida S, Rai T, Sasaki S, and Marumo F. Transcriptional regulation of aquaporin-2 water channel gene by cAMP. J Am Soc Nephrol 8:861-867, 1997

McHowat J and Creer M H. Thrombin activates a membrane-associated calcium-independent PLA2 in ventricular myocytes. Am J Physiol. Cell Physiol 274:C447-c454, 1998

Moses A M, Weinstock R S, Levine M A and Breslan N A. Evidence for normal antidiuretic response to endogenous and exogenous arginine vasopressin in patients with guanine nucleotide-binding stimulatory protein-deficient pseudohypo-parathyroiditis. J Clin Endocrinol Metab 62:221-224, 1986

Murray M D, and Brater D C. Renal toxicity of the non-steroidal anti-inflammatory drugs. Annun Rev Pharmacol Toxical 22:435-465, 1993

Murthy K S, Zhou H and Makhlouf G M. PKA-dependent activation of PDE3A and PDE4 and inhibition of adenylyl cyclase V/VI in smooth muscle. Am J Physiol. Cell Physiol 282:C508-C517, 2002

Nadler S P, Zimpelmann J A, and Hebert R L. PGE2 inhibits water permeability at a post-cAMP site in rat terminal inner medullary collecting duct. Am J Physiol. Renal Physiol 262:F229-f235, 1992

Nielsen S, DiGiovanni S R. Christensen E I, Knepper M A, and Harris H W. Cellular and subcellular immunolocalization of vasopressin-regulated water channel in rat kidney. Proc Natl Acad Sci. USA 90:11663-11667, 1993

Nielsen S, Chou C-L, Marples D, Chirstensen E I, Kishore B K, and Knepper M A. Vasopressin increases water permeability of kidney collecting duct by inducing translocation of aquaporin-CD water channels to plasma membrane. Proc Natl Acad Sci. USA 92:1013-1017, 1995

Nielsen S, Kwon T H, Christensen B M, Promeneur D, Frokiær J, and Marples D. Physiology and pathophysiology of renal aquaporins. J Am Soc Nephrol 10:647-663, 1999

Nishizukha Y. Intracellular signaling by hydrolysis of phospholipids and activation of protein kinase C. Science 258:607-614, 1992

Oksche A, and Rosenthal W. The molecular basis of nephrogenic diabetes insipidus. J Mol Med 75:326-337, 1998

Ostrom R S. Pst S R and Insel P A. Stoichiometry and compartmentation in G protein-coupled receptor signaling: implications for therapeutic interventions involving G(s). J Pharmacol Exp Ther 294:407-412, 2000

Phelan K M, Mosholder A D and Lu S. Lithium interaction with the cyclooxygenase 2 inhibitors rofecoxib and celecoxib and other nonsteroidsl anti-inflammatory drugs. J Clin Psychiatry 64:1328-1334, 2003

Rice W R, Burton F M, and Fiedeldey D T. Cloning and expression of the alveolar type II cell P2u-purinergic receptor. Am J Respir Cell Mol Biol 12:27-32, 1995

Roman R J, and Lechene C. Prostaglandin E2 and F2α-induced inhibition of AVP- and cAMP-stimulated $H_2O$, $Na^+$, and urea transport in rat IMCD. Am J Physiol. Renal Physiol 279:F294-F301, 2000

Roman R J and Lechene C. Prostaglandin E2 and F2α reduced urea reabsorption from the rat collecting duct. Am J Physiol Renal Fluid Electrolyte Physiol 241:F53-F60, 1981

Rouch A J, and Kudo L H. Role of PGE2 in α2-induced inhibition of AVP- and cAMP-stimulated $H_2O$, $Na^+$, and urea transport in rat IMCD. Am J Physiol: Renal Physiol 279:F294-F301, 2000

Rouse D, Leite M, and Suki W N. ATP inhibits the hydroosmotic effect of AVP in rabbit CCT: evidence for a nucleotide P2u receptor. Am J Physiol: Renal Physiol 267:F289-f295: 1994

Schwiebert E M, and Kishore B K, Extracellular nucleotide signaling along the renal epithelium. Am J Physiol. Renal Physiol 280:F945-F963, 2001

Sheikh-Hamad D, Cacini W, Buckley A R, Isaac J, Truong L D, Tsao C C, and Kishore B K. Cellular and molecular studies on cisplatin-induced apoptotic cell death in rat kidney. Arch Toxicol, 2003 [Epub]

Shoji Y, Takahashi M, Kitamura T, Watanabe K, Kawamori T, Maruyama T, Sugimoto Y, Negishi M, Narumiya S, Sugimura T and Wakabayashi K. Downregulation of prostaglandin E receptor subtype EP3 during colon cancer development. Gut 55; 1151-1158, 2004

Sonnenberg H, and Wilson D R. The role of the medullary collecting ducts in postobstructive diuresis. J Clin Invest 97:1564-1574, 1976

Sugawara M, Hashimot K, and Ota Z. Involvement of prostaglandin E2, cAMP, and vasopressin in lithium-induced polyuria. Am J Physiol. Regulatory Physiol 254: R863-R869, 1988

Sun R, Carlson N G, Hemmert A C, and Kishore B K. P2Y2 receptor-mediated release of prostaglandin E2 by IMCD is altered in hydrated and dehydrated rats: relevance to AVP-independent regulation of IMCD function. Am J Physiol, Renal Physiol 289:F585-F592, 2005a Sun E, Miller R L, Hemmert A C, Zhang P, Shi H, Nelson R D, and Kishore B K. Chronic dDAVP infusion in rats decreases the expression of P2Y2 receptor in inner medulla and P2Y2 receptor-mediated PGE2 by IMCD. Am J Physiol: Renal Physiol 289:F768-F776, 2005b Takeda S, Lin C-T, Morgano P G, McIntyre S J, and Dousa T P. High activity of low-Michaelis-Menton constant 3',5'-cyclic adenosine monophosphate-phosphodiesterase isozymes in renal inner medulla of mice with hereditary nephrogenic diabetes insipidus. Endocrinol 129:287-294, 1991

Teitelbaum I. Hormone signaling systems in inner medullary collecting ducts. Am J Physiol. Renal Physiol. 263:P985-F990, 1992

Terris J, Ecelberger C A, Nielsen S, and Knepper M A, Long-term regulation of four renal aquaporins in rats. Am J Physiol. Renal Physiol. 271:F414-F422, 1996

Timmer E T and Sands J M. Lithium intoxication. J Am Soc Nephrol 10:666-674, 1999

Wang W, Li C, kwon T-H, Knepper M A, Frøkiær J and Nielsen S. AQP3, p-AQP2, and AQP2 expression is reduced in polyuric rats with hypercalcemia: prevention by cAMP-PDE inhibitors. Am J Physiol, Renal Physiol 283:F1313-F1325, 2002

Welch B D, Carlson N G, Shi H, Myatt L, and Kishore B K. P2Y2 receptor-stimulated release of prostaglandin E2 by rat inner medullary collecting duct preparations. Am J Physiol. Renal Physiol. 285:P711-F721, 2003

William M. Purines: from premise to promise. J Auton Nerv Syst 81:285-288, 2000

Yang T, Schnermann J B and Briggs J P. Regulation of cyclooxygenase-2 expression in renal medulla by tonicity in vivo and in vitro. Am J Physiol 277:F1-F9, 1999

Yasui M, Zelenin S M, Celsi G and Aperia A. Adenylyl cyclase-coupled vasopressin receptor activates AQP2 promoter via a dual effect on CRE and API elements. Am J Physiol. 272:F442-F450, 1997

Zelenina M, Christensen B M, Palmer J, Narin A C, Nielsen S, and Aperia A. Prostaglandin E(2) interaction with AVP: effect of AQP2 phosphorylation and distribution. Am J Physiol. Renal Physiol 278:F388-F394, 2000

What is claimed is:

1. A method of treating nephrogenic diabetes insipidus (NDI) in a subject, comprising administering a composition to the subject, wherein the composition is an antagonist of a P2Y2 purinergic receptor.

2. The method of claim 1, wherein the antagonist is P2Y2 selective antagonist.

3. The method of claim 1, wherein the antagonist decreases the level of PGE2 in the kidney.

4. The method of claim 1, wherein the antagonist decreases the interaction of the P2Y2 receptor and PGE2.

5. The method of claim 1, wherein the P2Y2 antagonist is used in combination with inhibitors of prostaglandin synthesis.

6. The method of claim 5, wherein the inhibitor is a non-specific one for cyclooxygenases.

7. The method of claim 6, wherein the inhibitor is indomethacin, rofecoxib, or flurbiprofen.

8. The method of claim 6, wherein the inhibitor inhibits cyclooxygenase-1.

9. The method of claim 6, wherein the inhibitor inhibits cyclooxygenase-2.

10. The method of claim 1, wherein the P2Y2 antagonist is used in combination with a thiazide and optionally with an amiloride and/or a prostaglandin synthesis inhibitor.

11. The method of claim 1, wherein treating NDI in a subject comprises treating polyuria of the subject such that the subject has decreased urinary volume and increased urine osmolality.

12. The method of claim 11, wherein acquired NDI is selected from the group consisting of lithium-induced nephropathy, hypokalemic nephropathy, hypercalcemia-induced NDI, post-obstructive uropathy, chronic kidney disease-induced NDI, sickle cell disease-induced NDI, low protein diet-induced NDI and drug-induced NDI.

13. The method of claim 11, wherein acquired NDI is lithium-induced NDI.

14. The method of claim 11, wherein acquired NDI comprises polyuria comprising increased urinary volume and decreased urine osmolality.

15. The method of claim 11, wherein acquired NM comprises low protein levels of vasopressin-regulated water channel AQP2 in the medullary collecting duct, and additionally optionally comprising normal or elevated circulating levels of arginine vasopressin (AVP).

16. The method of claim 11, wherein acquired NDI comprises loss of sensitivity to downregulation of P2Y2 receptor expression in renal collecting duct by chronically elevated circulating AVP levels.

17. The method of claim 11, wherein acquired NDI comprises increased production or release of renal prostaglandin E2 (PGE2) by agonist-stimulated P2Y2 receptor.

18. The method of claim 17, wherein increased production or release of renal PGE2 results in inhibition of arginine vasopressin (AVP) action and wherein inhibition of AVP action comprises inhibition of AVP-induced water flow in renal collecting duct and AVP-induced trafficking of AQP2 water channel to apical plasma membrane of principal cell of renal collecting duct.

19. The method of claim 1, wherein NDI is acquired or inherited.

20. The method of claim 19, wherein the drug is selected from the group consisting of lithium, colchicine, methoxyflurane, amphotericin B, gentamicin, loop diuretics, and demeclocycline.

21. The method of claim 1, wherein the antagonist of a P2Y2 purinergic receptor is selected from the group consisting of suramin, reactive blue 2, acid blue 129, acid blue 80, and pyridoxalphosphate-6-azophenyl-2',4'-disulfonic acid (PPADS).

22. A method of modulating NDI in a subject, comprising administering a composition to the subject, wherein the composition is an antagonist of a P2Y2 purinergic receptor.

* * * * *

```
                          SEQUENCE LISTING

<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1
```

-continued

```
gggttgccat gtctcctttc cttcg                                          25

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
ccaggtcccc acggatttct                                                20

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct

<400> SEQUENCE: 3
acccgcaccc tctattactc cttc                                           24

<210> SEQ ID NO 4
<211> LENGTH: 24
<212> TYPE: DNA
<213> ORGANISM: Artificial Sequence
<220> FEATURE:
<223> OTHER INFORMATION: Synthetic Construct

<400> SEQUENCE: 4
agtagagcac agggtcaagg caac                                           24

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
ttgccttgat ggtgtttgtg                                                20

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
caccagactg gcgcgtgtat ct                                             22

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
gcacataata gtggaacacc                                                20

<210> SEQ ID NO 8
<211> LENGTH: 20
<212> TYPE: DNA
```

```
<213> ORGANISM: Artificial Sequence
<220> FEATURE:
<223> OTHER INFORMATION: Synthetic Construct

<400> SEQUENCE: 8
acacagtgcc atgctgaacc                                              20

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
taagtaccag gtgctggatg g                                            21

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
ggtttcccct ataaggatga g                                            21

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
tacaagcagt ggcaaaggcc                                              20

<210> SEQ ID NO 12
<211> LENGTH: 23
<212> TYPE: DNA
<213> ORGANISM: Artificial Sequence
<220> FEATURE:
<223> OTHER INFORMATION: Synthetic Construct

<400> SEQUENCE: 12
cagtattgag gagaacagat ggg                                          23

<210> SEQ ID NO 13
<211> LENGTH: 17
<212> TYPE: DNA
<213> ORGANISM: Artificial Sequence
<220> FEATURE:
<223> OTHER INFORMATION: Synthetic Construct

<400> SEQUENCE: 13
acgtccgtct gctggtc                                                 17

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
ccttctcctt tcccatctg                                               19
```

```
<210> SEQ ID NO 15
<211> LENGTH: 23
<212> TYPE: DNA
<213> ORGANISM: Artificial Sequence
<220> FEATURE:
<223> OTHER INFORMATION: Synthetic Construct

<400> SEQUENCE: 15
ctacatgttc cagtatgact cta                                          23

<210> SEQ ID NO 16
<211> LENGTH: 23
<212> TYPE: DNA
<213> ORGANISM: Artificial Sequence
<220> FEATURE:
<223> OTHER INFORMATION: Synthetic Construct

<400> SEQUENCE: 16
gagtggcagt gatggcatgg act                                          23

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
cactgtgttg gcatagaggt c                                            21

<210> SEQ ID NO 18
<211> LENGTH: 22
<212> TYPE: DNA
<213> ORGANISM: Artificial Sequence
<220> FEATURE:
<223> OTHER INFORMATION: Synthetic Construct

<400> SEQUENCE: 18
agagggaaat cgttgcgtga ca                                           22
```